US012766298B2

(12) United States Patent
Krishnan et al.

(10) Patent No.: US 12,766,298 B2
(45) Date of Patent: Oct. 20, 2026

(54) BIOELECTRONIC DEVICES TO SUPPORT TRANSPLANTED CELLS IN VIVO FOR ENCAPSULATED CELL THERAPIES

(71) Applicants: Massachusetts Institute of Technology, Cambridge, MA (US); The Children's Medical Center Corporation, Boston, MA (US)

(72) Inventors: Siddharth Krishnan, Cambridge, MA (US); Suman Bose, Cambridge, MA (US); Nima Khatib, Somerville, MA (US); Matthew Bochenek, Cambridge, MA (US); Robert S. Langer, Newton, MA (US); Daniel Anderson, Framingham, MA (US)

(73) Assignees: Massachusetts Institute of Technology, Cambridge, MA (US); The Children's Medical Center Corporation, Boston, MA (US)

( * ) Notice: Subject to any disclaimer, the term of this patent is extended or adjusted under 35 U.S.C. 154(b) by 1194 days.

(21) Appl. No.: 17/738,200

(22) Filed: May 6, 2022

(65) Prior Publication Data

US 2023/0017523 A1 Jan. 19, 2023

Related U.S. Application Data

(60) Provisional application No. 63/218,734, filed on Jul. 6, 2021.

(51) Int. Cl.

*A61M 37/00* (2006.01)
*A61K 9/00* (2006.01)

(Continued)

(52) U.S. Cl.

CPC ........... *A61M 37/00* (2013.01); *A61K 9/0024* (2013.01); *A61K 35/22* (2013.01); *A61K 35/39* (2013.01);

(Continued)

(58) Field of Classification Search

CPC .......... A61M 37/00; A61M 2202/0208; A61M 2202/09; A61M 2205/0238;

(Continued)

(56) References Cited

U.S. PATENT DOCUMENTS 3,878,564 A * 4/1975 Yao .................... A61M 1/3687 604/28
6,368,592 B1 4/2002 Colton et al.

(Continued)

FOREIGN PATENT DOCUMENTS

KR 101978380 B1 5/2019
WO 9955360 A1 11/1999

OTHER PUBLICATIONS

"Our Issued Patents" from Giner Life Sciences website accessed at: https://www.ginerinc.com/life-sciences-patents 2022, 2 pages.

(Continued)

*Primary Examiner* — Nilay J Shah
(74) *Attorney, Agent, or Firm* — Eversheds Sutherland (US) LLP

(57) ABSTRACT

A bioelectronic device houses therapeutic cells and is configured to be implanted in a host. The device includes an electrochemical cell that produces oxygen gas from water when a voltage is applied. The oxygen gas produced by the electrochemical cell is stored in a gas diffusion chamber in the device. The therapeutic cells in a cell housing chamber in the device receive oxygen gas from the gas diffusion chamber to help keep the cells alive and functioning when (Continued)

the device is implanted in a low oxygen environment. The device receives power wirelessly.

19 Claims, 27 Drawing Sheets

(51) Int. Cl.
*A61K 35/22* (2015.01)
*A61K 35/39* (2015.01)
*C25B 1/04* (2021.01)

(52) U.S. Cl.
CPC ....... *C25B 1/04* (2013.01); *A61M 2202/0208* (2013.01); *A61M 2202/09* (2013.01); *A61M 2205/0238* (2013.01); *A61M 2205/051* (2013.01); *A61M 2205/3303* (2013.01); *A61M 2205/8206* (2013.01); *A61M 2207/00* (2013.01)

(58) Field of Classification Search
CPC .... A61M 2205/051; A61M 2205/3303; A61M 2205/8206; A61F 2/022
See application file for complete search history.

(56) References Cited

U.S. PATENT DOCUMENTS

| | | | | |
|---|---|---|---|---|
| 7,892,222 | B2 * | 2/2011 | Vardi | A61F 2/022 604/93.01 |
| 8,444,630 | B2 * | 5/2013 | Rotem | A61F 2/022 604/500 |
| 10,231,817 | B2 | 3/2019 | Tempelman et al. | |
| 10,557,691 | B2 | 2/2020 | Stone et al. | |
| 2003/0087427 | A1 | 5/2003 | Colton et al. | |
| 2004/0267189 | A1 * | 12/2004 | Mavor | A61N 1/044 604/20 |
| 2005/0136092 | A1 | 6/2005 | Rotem et al. | |
| 2007/0298069 | A1 | 12/2007 | Bucay-Couto et al. | |
| 2010/0330547 | A1 | 12/2010 | Tempelman et al. | |
| 2017/0303838 | A1 * | 10/2017 | Brill | G01N 21/6428 |
| 2018/0133383 | A1 | 5/2018 | Ferrante et al. | |
| 2018/0135948 | A1 | 5/2018 | Stone et al. | |
| 2019/0336267 | A1 * | 11/2019 | Tempelman | A61F 2/022 |
| 2019/0343616 | A1 | 11/2019 | Stone | |
| 2019/0368056 | A1 | 12/2019 | Schwenk et al. | |

OTHER PUBLICATIONS

BetaO2 website "Welcome to Beta-O2 Technologies" accessed at https://beta-02.com/ 2022 3 pages.
Bhatia et al. "Microfluidic organs-on-chips." Nature biotechnology 32.8 (2014): 760-772.
Bose et al. "A retrievable implant for the long-term encapsulation and survival of therapeutic xenogeneic cells." Nature biomedical engineering 4.8 (2020): 814-826.
Bristow et al. "Hypoxia, DNA repair and genetic instability." Nature Reviews Cancer 8.3 (2008): 180-192.
Chang et al. "Nanoporous immunoprotective device for stem-cell-derived β-cell replacement therapy." ACS nano 11.8 (2017): 7747-7757.
Colton "Oxygen supply to encapsulated therapeutic cells." Advanced drug delivery reviews 67 (2014): 93-110.
Diandreth et al. "PERSIST: a programmable RNA regulation platform using CRISPR endoRNases." BioRxiv (2019), 19 pages.
Farah et al. "Long-term implant fibrosis prevention in rodents and non-human primates using crystallized drug formulations." Nature materials 18.8 (2019): 892-904.
Gaidukov et al. "A multi-landing pad DNA integration platform for mammalian cell engineering." Nucleic acids research 46.8 (2018): 4072-4086.
Gardeniers et al. "Silicon micromachined hollow microneedles for transdermal liquid transport." Journal of Microelectromechanical systems 12.6 (2003): 855-862.
Gutruf et al. "Fully implantable optoelectronic systems for battery-free, multimodal operation in neuroscience research." Nature Electronics 1.12 (2018): 652-660.
Gutruf et al. "Implantable, wireless device platforms for neuroscience research." Current opinion in neurobiology 50 (2018): 42-49.
Henry et al. "Microfabricated microneedles: a novel approach to transdermal drug delivery." Journal of pharmaceutical sciences 87.8 (1998): 922-925.
Hofmann et al. "Epigenetic regulation of lentiviral transgene vectors in a large animal model." Molecular Therapy 13.1 (2006): 59-66.
Huang et al. "Engineering light-controllable CAR T cells for cancer immunotherapy." Science advances 6.8 (2020): eaay9209, 14 pages.
Huh et al. "Microengineered physiological biomimicry: organs-on-chips." Lab on a Chip 12.12 (2012): 2156-2164.
Iwamoto et al. "A general chemical method to regulate protein stability in the mammalian central nervous system." Chemistry & biology 17.9 (2010): 981-988.
Kauper et al. "Two-year intraocular delivery of ciliary neurotrophic factor by encapsulated cell technology implants in patients with chronic retinal degenerative diseases." Investigative ophthalmology & visual science 53.12 (2012): 7484-7491.
Kim et al. "Biomolecular strategies to modulate the macrophage response to implanted materials." Journal of Materials Chemistry B 4.9 (2016): 1600-1609.
Kim et al. "Human gut-on-a-chip inhabited by microbial flora that experiences intestinal peristalsis-like motions and flow." Lab on a Chip 12.12 (2012): 2165-2174.
Kim et al. "Microneedles for drug and vaccine delivery." Advanced drug delivery reviews 64.14 (2012): 1547-1568.
Konermann et al. "Optical control of mammalian endogenous transcription and epigenetic states." Nature 500.7463 (2013): 472-476.
Li et al. "Conical nanopore membranes. Preparation and transport properties." Analytical chemistry 76.7 (2004): 2025-2030.
Lu et al. "Biodegradable monocrystalline silicon photovoltaic microcells as power supplies for transient biomedical implants." Advanced Energy Materials 8.16 (2018) 1703035, 8 pages.
Ludwig et al. "Favorable outcome of experimental islet xenotransplantation without immunosuppression in a nonhuman primate model of diabetes." Proceedings of the National Academy of Sciences 114.44 (2017): 11745-11750.
Miyazaki et al. "Destabilizing domains derived from the human estrogen receptor." Journal of the American Chemical Society 134.9 (2012): 3942-3945.
Montefiori et al. "Complement control proteins, CD46, CD55, and CD59, as common surface constituents of human and simian immunodeficiency viruses and possible targets for vaccine protection." Virology 205.1 (1994): 82-92.
Nyitray et al. "Polycaprolactone thin-film micro- and nanoporous cell-encapsulation devices." ACS nano 9.6 (2015): 5675-5682.
Parada et al. "Ultrathin and robust hydrogel coatings on cardiovascular medical devices to mitigate thromboembolic and infectious complications." Advanced Healthcare Materials 9.20 (2020): 2001116, 9 pages.
Park et al. "Soft, stretchable, fully implantable miniaturized optoelectronic systems for wireless optogenetics." Nature biotechnology 33.12 (2015): 1280-1286.
Pasi et al. "Multiyear follow-up of AAV5-hFVIII-SQ gene therapy for hemophilia A." New England Journal of Medicine 382.1 (2020): 29-40.
Patel et al. "Electrochemical properties of nanostructured porous gold electrodes in biofouling solutions." Analytical chemistry 85.23 (2013): 11610-11618.
Pedraza et al. "Preventing hypoxia-induced cell death in beta cells and islets via hydrolytically activated, oxygen-generating biomaterials." Proceedings of the National Academy of Sciences 109.11 (2012): 4245-4250.
Polesskaya et al. "Optogenetic regulation of transcription." BMC neuroscience 19.1 (2018): 3-13.

(56) References Cited

OTHER PUBLICATIONS

Prausnitz "Microneedles for transdermal drug delivery." Advanced drug delivery reviews 56.5 (2004): 581-587.
Redchuk et al. "Near-infrared optogenetic pair for protein regulation and spectral multiplexing." Nature chemical biology 13.6 (2017): 633-639.
Robb "Thin silicone membranes—their permeation properties and some applications." Annals of the New York Academy of Sciences 146.1 (1968): 119-137.
Schweicher et al. "Membranes to achieve immunoprotection of transplanted islets." Frontiers in bioscience (Landmark edition) 19 (2014): 49-76.
Sigilon Therapeutics website "Shielded Living Therapeutics" accessed at: https://sigilon.com/ 2022 3 pages.
Smith et al. "Vascular catheters with a nonleaching poly-sulfobetaine surface modification reduce thrombus formation and microbial attachment." Science translational medicine 4.153 (2012): 153ra132-153ra132, 11 pages.
Tatsumi et al. "Perioperative haemostatic management of haemophilic mice using normal mouse plasma." Haemophilia 19.6 (2013): e335-e343.
Teo et al. In vitro and in vivo characterization of MEMS microneedles. Biomedical microdevices 7.1 (2005): 47-52.
Towards advanced cell therapies. Nature Biomedical Engineering. Jun. 11, 2018;2(6):339-40.
Upadhyayula et al. "Appreciating the role of carbon nanotube composites in preventing biofouling and promoting biofilms on material surfaces in environmental engineering: a review." Biotechnology advances 28.6 (2010): 802-816.
Vegas et al. "Combinatorial hydrogel library enables identification of materials that mitigate the foreign body response in primates." Nature biotechnology 34.3 (2016): 345-352.
Vegas et al. "Long-term glycemic control using polymer-encapsulated human stem cell-derived beta cells in immune-competent mice." Nature medicine 22.3 (2016): 306-311.
ViaCyte website home page accessed at https://viacyte.com/ on Aug. 19, 2022, 1 page.
Voskerician et al. "Biocompatibility and biofouling of MEMS drug delivery devices." Biomaterials 24.11 (2003): 1959-1967.
Wagner et al. "The rate of oxygen utilization by cells." Free Radical Biology and Medicine 51.3 (2011): 700-712.
International Search Report and Written Opinion in International Application No. PCT/US2022/028000 mailed Aug. 15, 2022, 10 pages.
Ward "A review of the foreign-body response to subcutaneously-implanted devices: the role of macrophages and cytokines in biofouling and fibrosis." Journal of diabetes science and technology 2.5 (2008): 768-777.
Whitesides "The origins and the future of microfluidics." Nature 442.7101 (2006): 368-373.
Whyte et al. "Sustained release of targeted cardiac therapy with a replenishable implanted epicardial reservoir." Nature Biomedical Engineering 2.6 (2018): 416-428.
Wikstrom et al. "Alginate-based microencapsulation of retinal pigment epithelial cell line for cell therapy." Biomaterials 29.7 (2008): 869-876.
Wu et al. "In situ electrochemical oxygen generation with an immunoisolation device." Annals of the new York Academy of Sciences 875.1 (1999): 105-125.
Xie et al. "Reduction of measurement noise in a continuous glucose monitor by coating the sensor with a zwitterionic polymer." Nature biomedical engineering 2.12 (2018): 894-906.
Zhang et al. "Zwitterionic hydrogels implanted in mice resist the foreign-body reaction." Nature biotechnology 31.6 (2013): 553-556.

* cited by examiner

Sectioned Side View

Top View

BIOELECTRONIC DEVICES TO SUPPORT TRANSPLANTED CELLS IN VIVO FOR ENCAPSULATED CELL THERAPIES

CROSS-REFERENCE TO RELATED APPLICATION(S)

This application claims the priority benefit, under 35 U.S.C. 119(e), of U.S. Application No. 63/218,734, filed Jul. 6, 2021, entitled "BIOELECTRONIC DEVICES TO SUPPORT TRANSPLANTED CELLS IN VIVO FOR ENCAPSULATED CELL THERAPIES," which is incorporated herein by reference in its entirety for all purposes.

GOVERNMENT SUPPORT

This application was made with Government support under Grant No. K99 EB025254 awarded by the National Institutes of Health (NIH). The Government has certain rights in the invention.

BACKGROUND

Proteins and biologics are therapeutics for a range of diseases. Prevalent chronic diseases such as diabetes, anemia and clotting disorders are treated by replenishing defective or deficient proteins. Antibodies and cytokines form the basis for cancer immunotherapy. New protein therapeutics have shown great promise in treating Parkinson's and Huntington's disease and have recently entered clinical trials. Despite their efficacy, long-term delivery of these macromolecules remains a challenge, and direct injection into patients still serves as the primary route of administration. There is a need to develop technologies that can deliver therapeutic proteins for the treatment of chronic conditions. While in vivo gene delivery and genome editing has the potential to correct genetic deficiencies, there are several practical limitations to this approach. Delivery of genetic material to cells is inefficient in vivo, viral vectors like adeno-associated virus (AAV) can contain only a limited amount of genetic information and hence are not suitable for producing larger proteins, there is risk of off-targeting effects in cells, and often the fate of the therapy is directed by the immune reaction to the virus or transformed cells. In contrast, cell-based therapies, where exogenous cells, either natural or engineered to secrete desired proteins, are grafted into the body represent attractive options in long-term, continuous protein delivery. Primary cells sourced from human donor organs and transplanted in patients can take over functions of entire failing organs. Advances in stem cell technology have made it possible to generate unlimited quantities of functionally differentiated cells and organoids including pancreatic β-cells and neurons, suggesting pathways for developing long-term cures for diseases such as diabetes and neurological degeneration. Unlike gene delivery which currently only treats monogenic diseases, engineered cells harboring synthetic gene circuits could perform sophisticated functions and deliver precisely controlled doses of therapeutics on-demand, allowing treatment of complex diseases such as diabetes and autoimmune disorders.

Engineered therapeutic cells hold great promise as cost-effective therapies for several chronic disorders. However, these cells can be immunogenic to the host and their broad application has been limited by the use of immunosuppressants in patients. Devices which can immune-isolate cells and allow the cells to function have emerged as a promising strategy to transplant these cells without chronic immunosuppression. For example, immune-isolating devices have been developed that physically separate the cells from the host immune system while facilitating the passive diffusion of oxygen and nutrients from the host to the cells. Devices that incorporate large numbers of cells, sufficient for therapeutic levels of protein secretion, (sometimes called 'macrodevices') have attracted attention owing to their retrievability, clinical promise and safety profiles. Unfortunately, despite decades of intense research, the goal of developing an immune isolating device that remains functional in humans over the long term has yet to be realized.

SUMMARY

A device for implantation in a subject may include an electrochemical cell, a circuit electrically coupled to the electrochemical cell, a chamber coupled to the electrochemical cell, and a reservoir configured to hold a set of biological entities. The electrochemical cell is configured to produce oxygen gas from water when a voltage is applied across the electrochemical cell. The electrochemical cell includes a cathode, an anode, and a first membrane disposed between the cathode and the anode. The first membrane is configured to permit passage of cations therebetween. The circuit is configured to provide power to the electrochemical cell and to receive power wirelessly from a remote device. The chamber is configured to receive at least a portion of the oxygen gas produced by the electrochemical cell. The reservoir is configured to receive oxygen gas from the chamber for consumption by the set of biological entities. A second membrane forms a portion of the reservoir. The second membrane is permeable to one or more substances generated by the set of biological entities for delivery of the substances to the subject via the second membrane.

The circuit may include a circuit board. The circuit board may include at least two bond pads disposed thereon. The circuit may be electrically coupled to the electrochemical cell via conductive adhesive bonding between at least part of a surface of the cathode and a first bond pad, and at least part of a surface of the anode and a second bond pad. The circuit may also include at least one light-emitting diode disposed on the circuit board and optically coupled to the reservoir. The light-emitting diode may be configured to generate a light beam to enhance or modulate a function of the set of biological entities. The circuit may also include a microcontroller disposed on the circuit board and configured to modulate a pulse intensity, a pulse frequency, a duty cycle, or a combination thereof, of the at least one light-emitting diode. The at least one light-emitting diode may include a plurality of light-emitting diodes optically coupled to the reservoir. The microcontroller may be configured to multiplex the plurality of light-emitting diodes to sequentially address individual light-emitting diodes of the plurality of light-emitting diodes. The circuit may also include a rechargeable battery. The microcontroller and the battery may be collectively configured to store the received power to the battery and to provide the power stored in the battery to the electrochemical cell.

The device may also include an oxygen sensor disposed in the reservoir or chamber and communicably coupled to the microcontroller. The microcontroller may further be configured to modulate operation of the at least one light-emitting diode to maintain, based on an oxygen level detected by the oxygen sensor, the oxygen level in the reservoir or chamber within a predetermined range.

The device may also include a coating disposed on at least the second membrane. The coating may include an anti-fibrotic substance. The coating may include a zwitterionic compound to prevent or mitigate an accumulation of immune cells, formation of scar tissue, or both. The zwitterionic compound may include at least one of sulfobetaine or phosphocholine polymer modified with at least one of tetrahydropyran phenyl triazole (THPT), (4-(4-(((tetrahydro-2H-pyran-2-yl)oxy)methyl)-1H-1,2,3-triazol-1-yl) phenyl) phenyl triazole, or N-(4-((1,1-dioxidothiomorpholino)methyl)-1H-1,2,3-triazol-1-yl).

The second membrane may be permeable to oxygen and nutrients. The second membrane may include at least one of polydimethylsiloxane or polycarbonate. The second membrane may include a plurality of pores having a surface coverage of at least 5% of a total surface area of the second membrane, each pore of the plurality of pores independently having a pore diameter of from about 20 nm to about 5 μm.

The chamber may include at least one port to provide fluid communication between a fluid within the chamber and a biological fluid of the subject. In another version, the chamber may include liquid water disposed therein and the chamber may be sealed to prevent fluid communication with fluids outside the chamber. The device may not include a battery or an external oxygen supply. The chamber may be configured to maintain an oxygen partial pressure of about 30 kilopascals to about 50 kilopascals during operation. The anode and the cathode may each comprise at least one of platinum, gold, carbon, iridium, or an oxygen-containing compound.

The set of biological entities may include at least one of primary human cells, stem cell derived cells, cell lines, or xenogeneic cells. The primary human cells may include at least one of hepatocytes, islets, mesenchymal stem cells, human dermal fibroblasts, or neurons. The cell lines may include at least one of Human Embryonic Kidney (HEK) cells, ARPE cells, or CHO-K1 cells. The xenogeneic cells may include pancreatic islets.

A method of making a device for implantation in a subject includes forming a cathode and an anode on either side of a first membrane to fabricate an electrochemical cell, coupling the cathode and the anode to a circuit, forming a chamber disposed on the electrochemical cell, forming a reservoir disposed on the chamber, and covering at least the second membrane with a coating including an anti-fibrotic substance. The first membrane is configured to permit passage of cations between the anode and the cathode, such that during use the electrochemical cell produces oxygen gas from water upon application of a voltage between the anode and the cathode. The circuit is configured to provide power to the electrochemical cell and receive power wirelessly from a remote device. The chamber is configured to receive at least a portion of the oxygen gas produced by the electrochemical cell. The reservoir holds a set of biological entities and is configured to receive oxygen gas from the chamber. The reservoir includes a second membrane forming a portion of the reservoir such that the membrane interfaces with the subject. The second membrane is permeable to one or more substances generated by the set of biological entities for delivery of the one or more substances to the subject via the second membrane.

A method of administering a substance to a subject using a device implanted in the subject includes delivering power wirelessly to a circuit of the device, and applying a voltage across the electrochemical cell of the device via the circuit to generate oxygen gas, such that generated oxygen gas diffuses from the electrochemical cell, through the chamber of the device, and into the reservoir of the device for consumption by the set of biological entities disposed therein, resulting in generation of the substance by the biological entities and subsequent diffusion of the substance across the membrane and the coating for delivery to the subject. The device includes the electrochemical cell configured to produce oxygen gas from water vapor when a voltage is applied across the electrochemical cell. The device also includes the circuit electrically coupled to the electrochemical cell and configured to provide power to the electrochemical cell. The circuit is configured to receive power wirelessly from a remote device. The device also includes the chamber coupled to the electrochemical cell. The chamber is configured to receive at least a portion of the oxygen gas produced by the electrochemical cell. The device also includes the reservoir configured to hold a set of biological entities and receive oxygen gas from the chamber. The reservoir includes a membrane forming a portion of the reservoir. The membrane is permeable to one or more substances generated by the set of biological entities for delivery of the one or more substances to the subject via the membrane. The device also includes the coating disposed on at least one outer surface of the device. The coating includes an anti-fibrotic substance.

A method of implanting a device in a subject includes inserting the device into at least one of a subcutaneous space of the subject or an intraperitoneal space of the subject.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. The terminology used herein that also may appear in any disclosure incorporated by reference should be accorded a meaning most consistent with the particular concepts disclosed herein.

BRIEF DESCRIPTIONS OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally and/or structurally similar elements).

FIG. 5B shows a method for adding an anti-fibrotic coating to the bioelectronic device in

FIG. 5A.

Figure 5A:
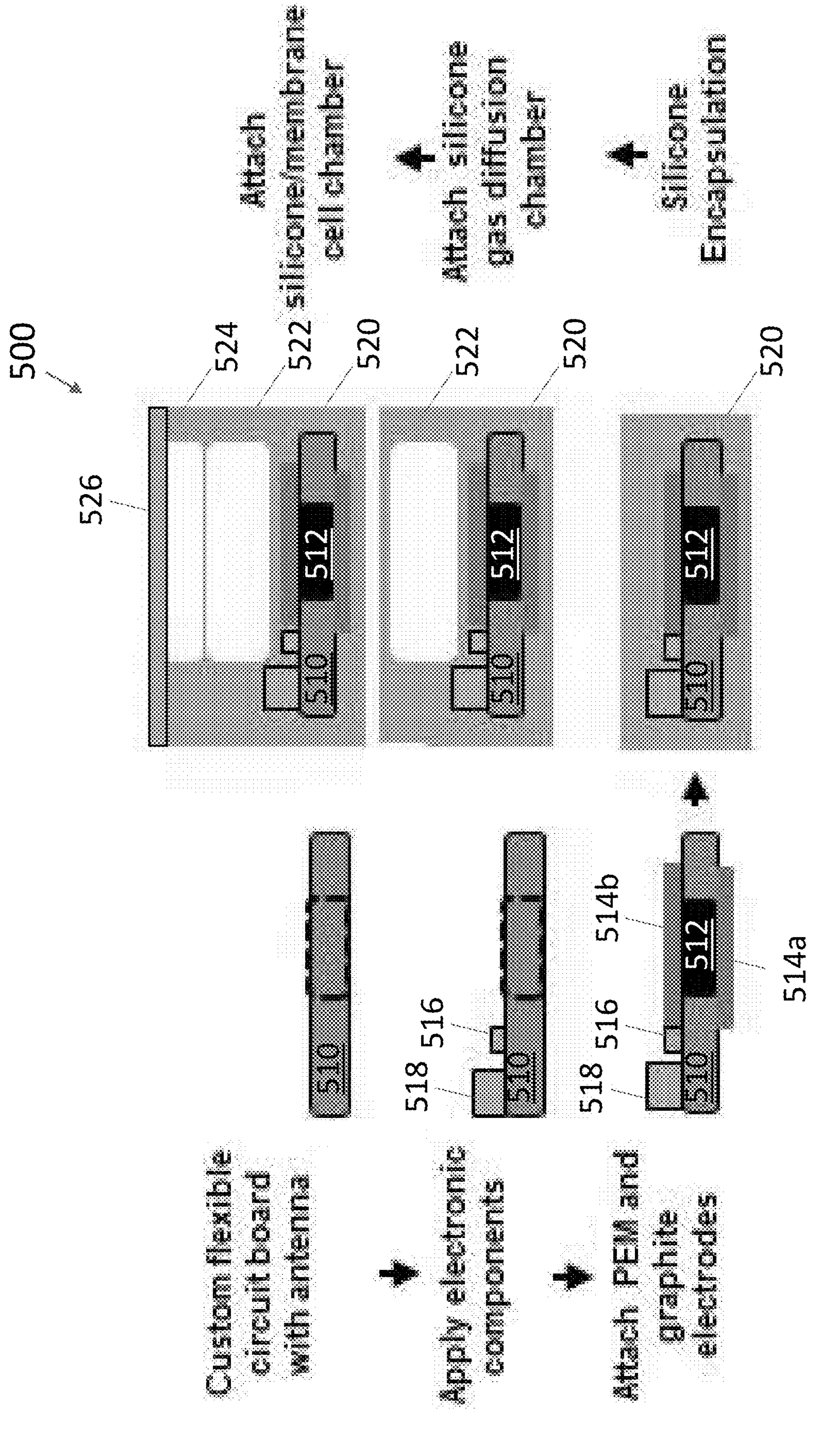
FIG. 5A shows a method for making a bioelectronic device for encapsulated cell therapies.
Figure 5B:
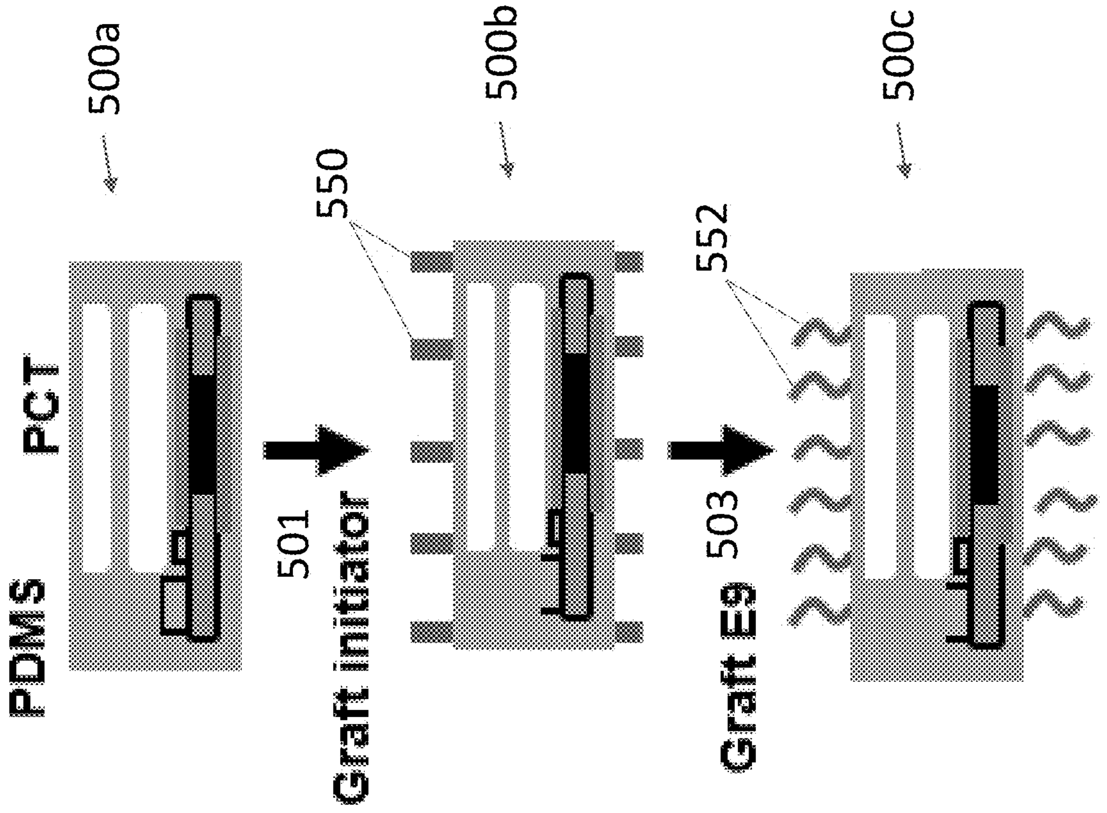
Figure 5C:
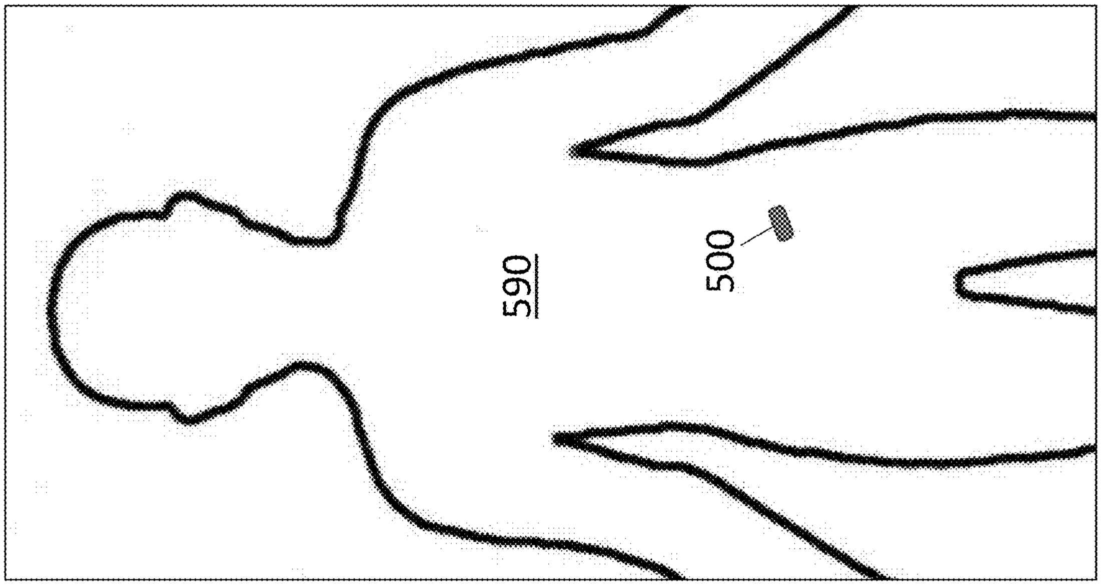

FIG. 5C shows an example placement of the bioelectronic device for encapsulated cell therapies in a patient.

Figure 6A:
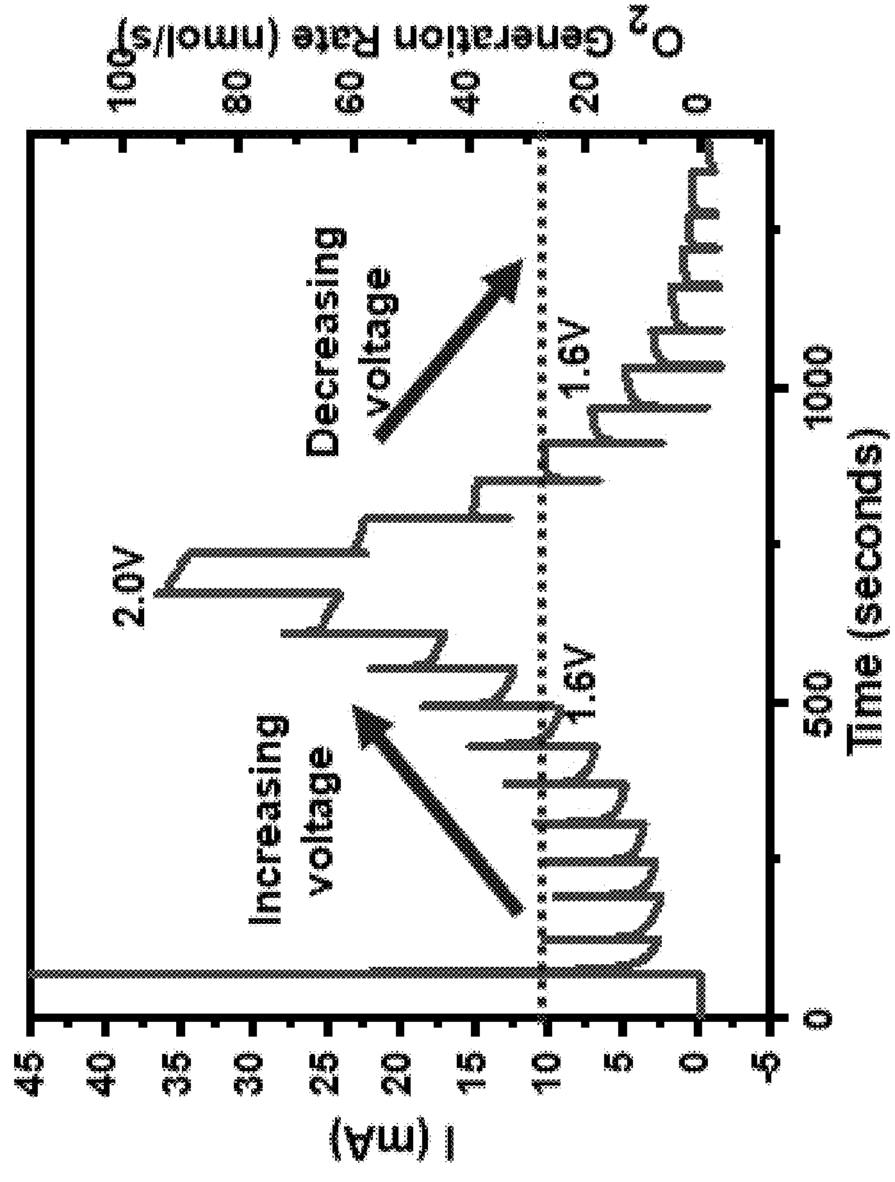

FIG. 6A is a plot illustrating current measured during a voltage sweep of the electrochemical cell in a bioelectronic device with calculated $O_2$ generation rates varying with voltage from 1.2 V to 2.0 V. The dashed line represents the $O_2$ consumption rate (OCR) estimated for a therapeutic dose of islets in an adult human.

Figure 6B:
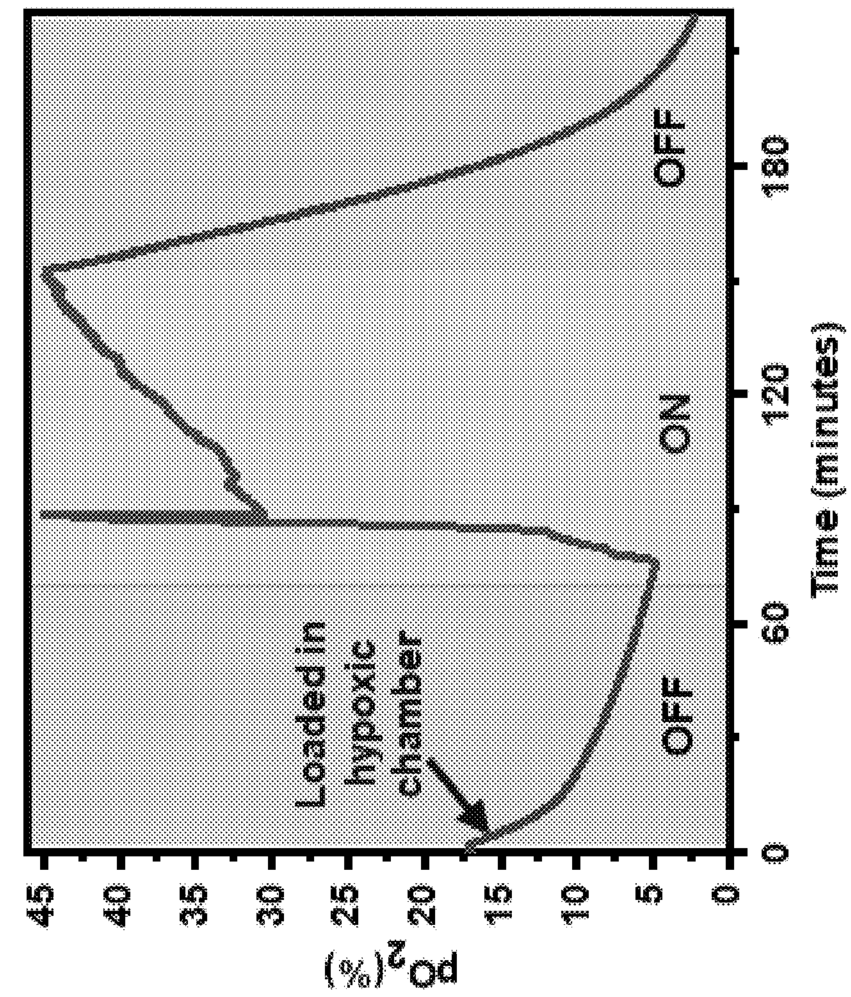

FIG. 6B is a plot illustrating $O_2$ concentrations measured by an optical sensor above an electrochemical stack for a bioelectronic device placed in a chamber having 5% $O_2$ (a hypoxic condition) and subsequent operation of the bioelectronic device at 2 V.

Figure 1A:
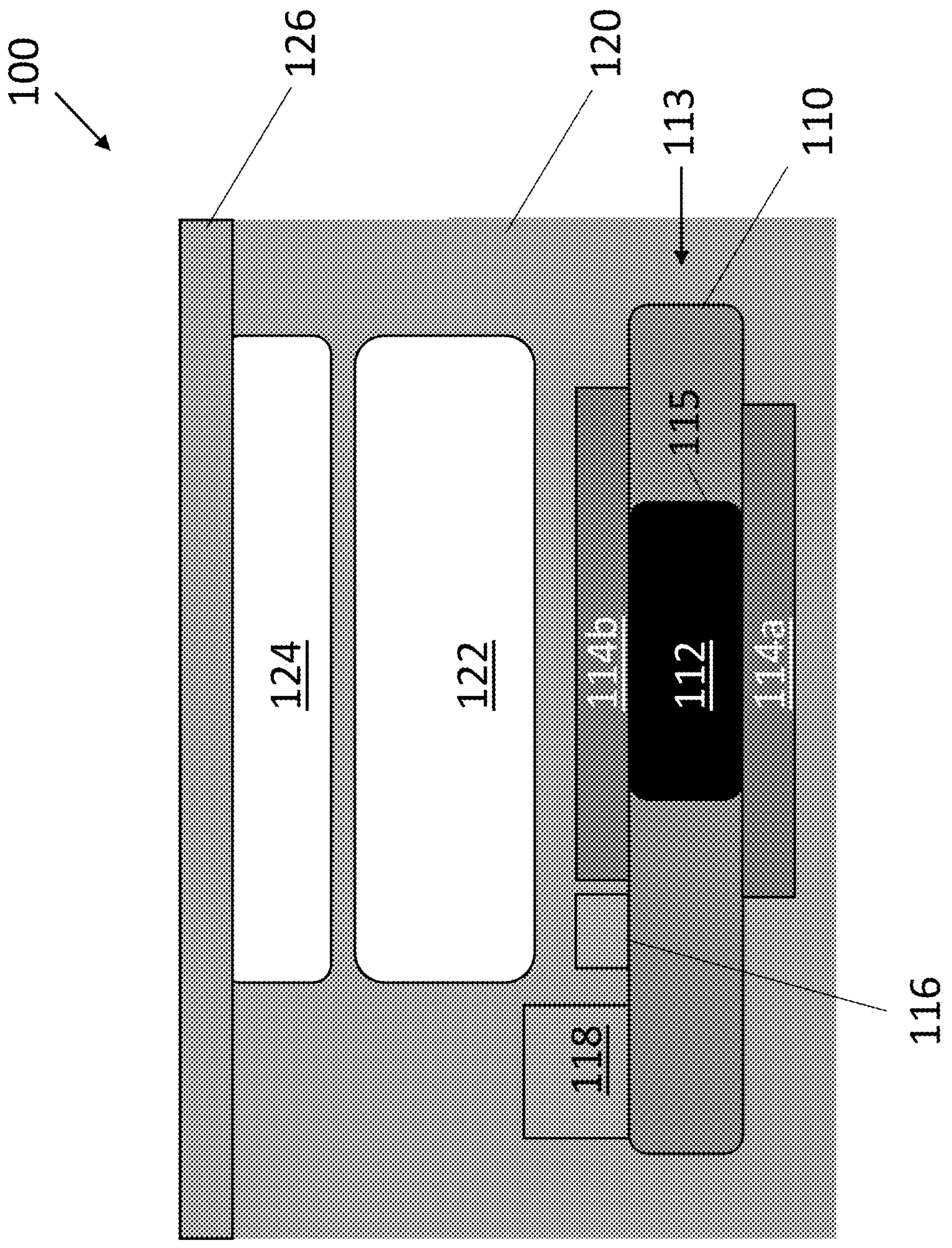
FIG. 1A illustrates a cross-sectional view of a bioelectronic device for encapsulated cell therapies.
Figure 7A:
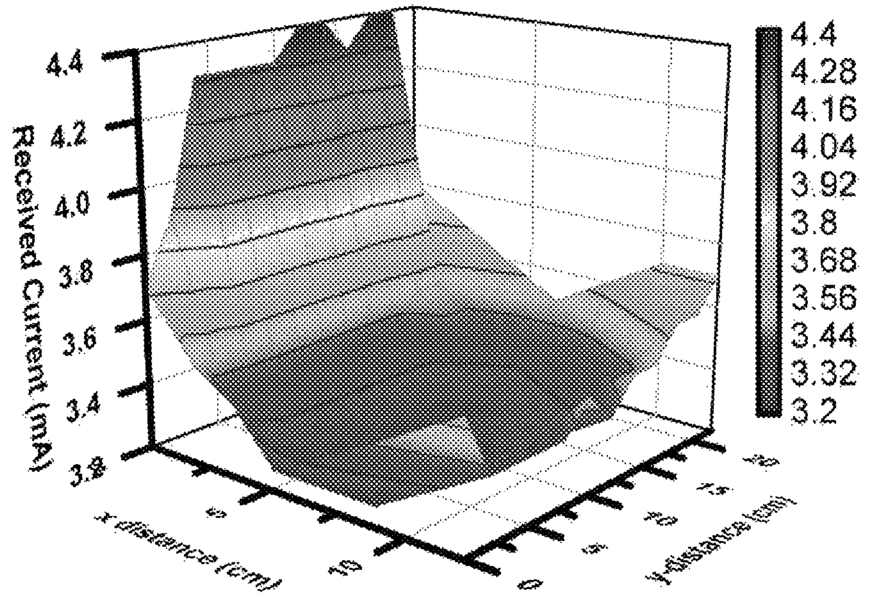

FIG. 7A is a plot illustrating measurements of current received by the bioelectronic device in FIG. 1A across a standard mouse enclosure (10 cm×22 cm) at a height of 3.7 cm corresponding to animal height at a load of 1000 ohm.

Figure 7B:
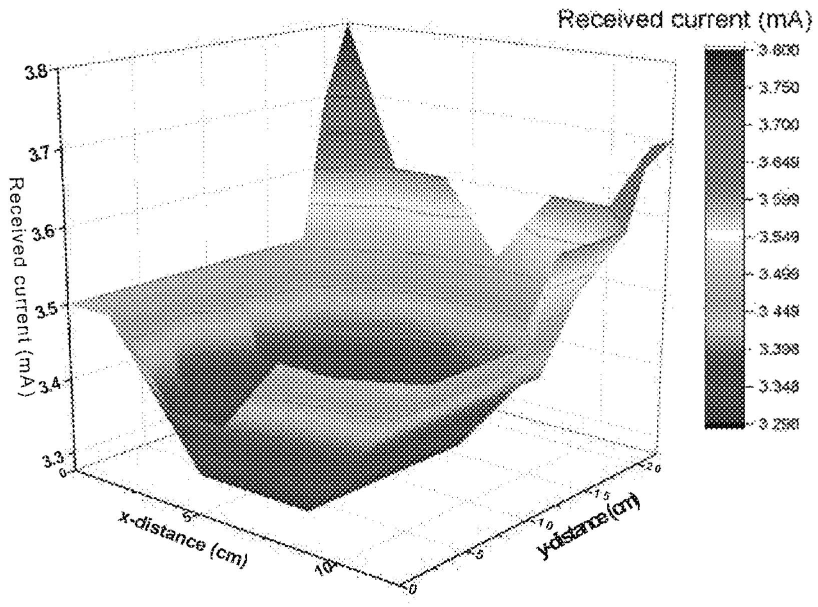

FIG. 7B is a plot illustrating measurements of current received by the bioelectronic device in FIG. 1A across a standard mouse enclosure (10 cm×22 cm) at a height of 4.8 cm corresponding to animal height at a load of 1000 ohm.

Figure 7C:
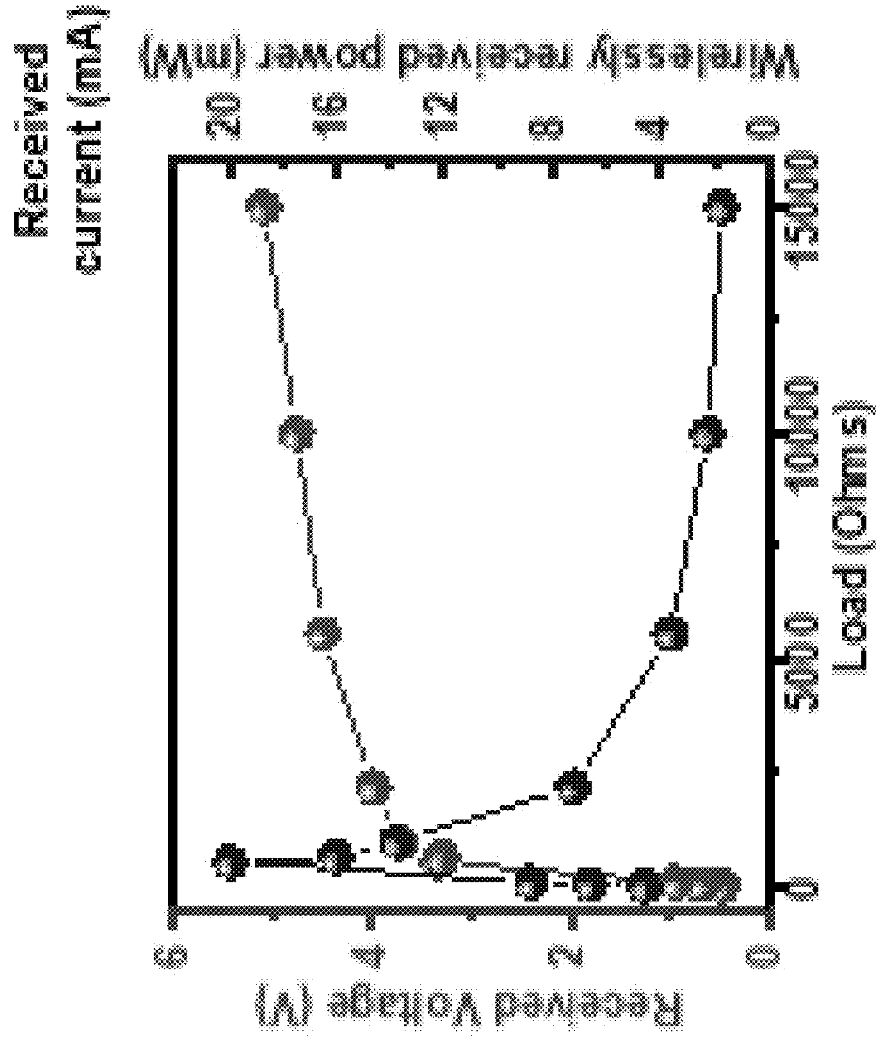

FIG. 7C is a plot illustrating measurements of received voltage and power using an inductor on the bioelectronic device in FIG. 1A as a function of load.

Figure 7D:
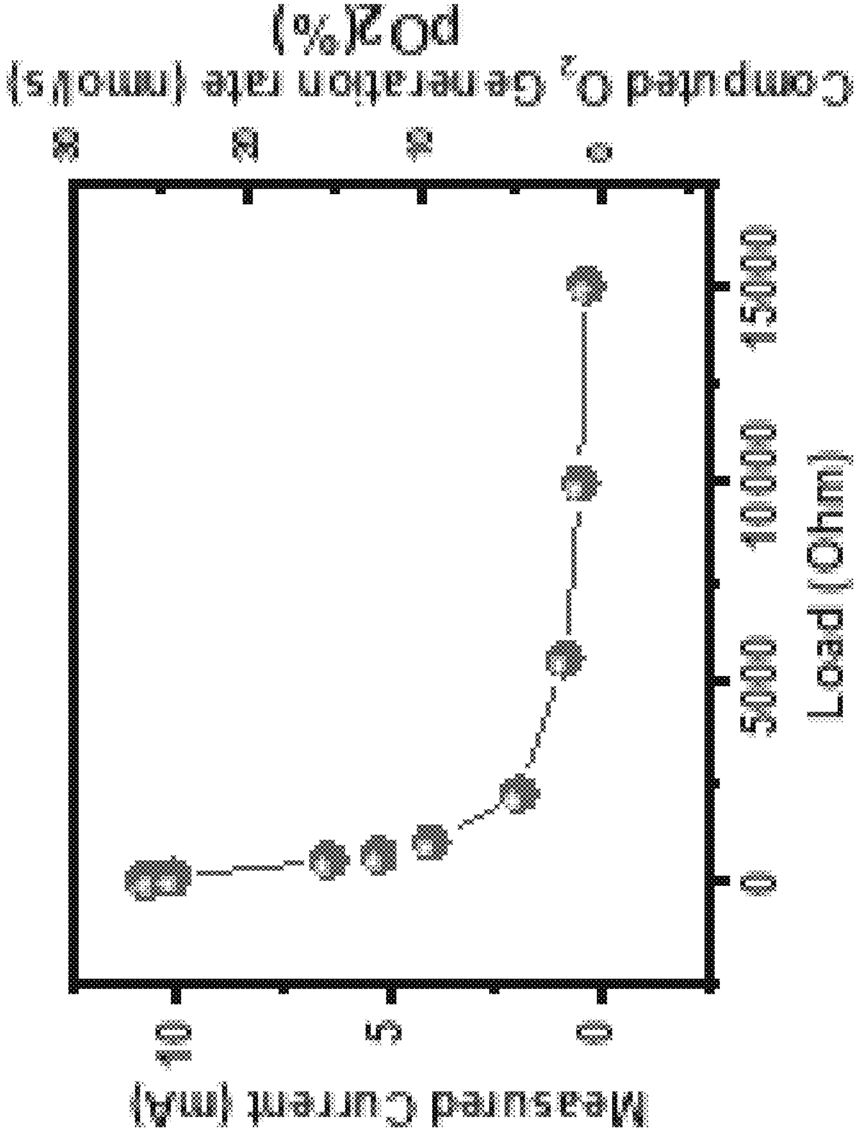

FIG. 7D is a plot illustrating measured current and computed oxygen production by the bioelectronic device in FIG. 1A at different current values as a function of load.

Figure 7E:
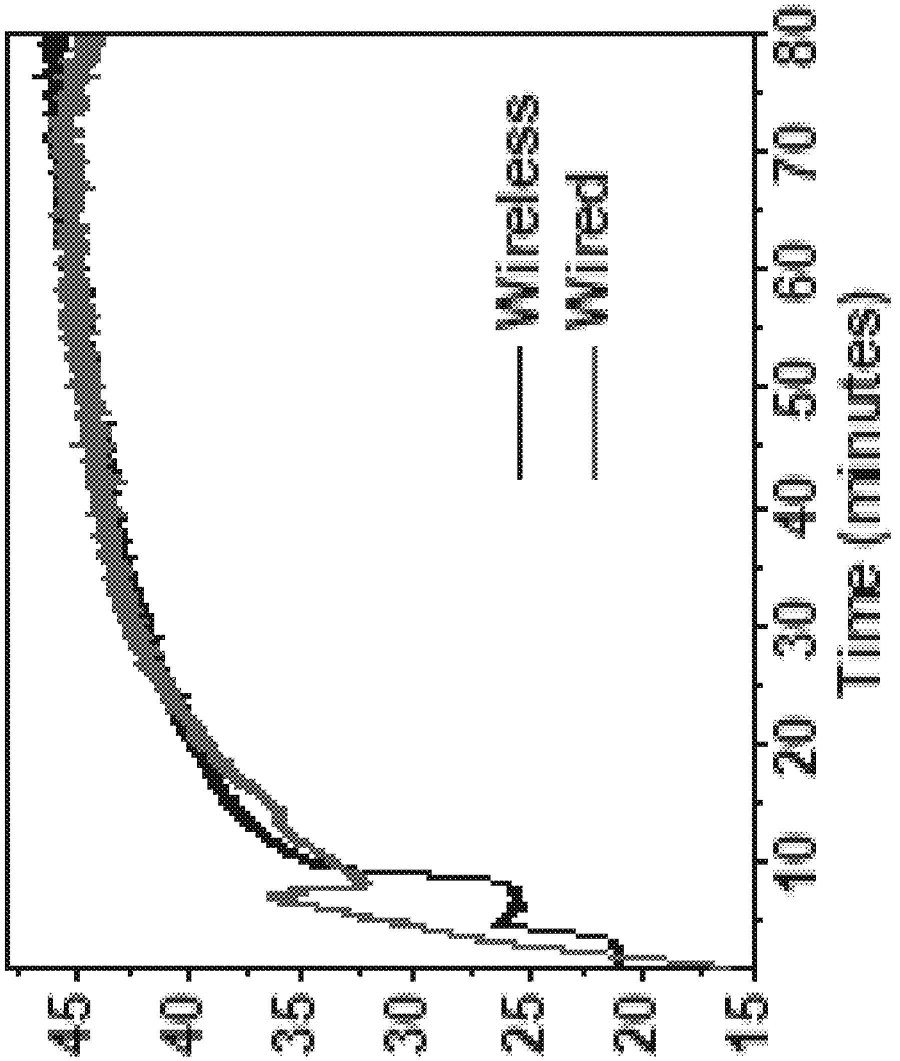

FIG. 7E is a plot illustrating $O_2$ production rates of wired and wireless embodiments of the bioelectronic device in FIG. 1A as measured with a commercially available $O_2$ sensor in gas diffusion chamber.

Figure 7F:
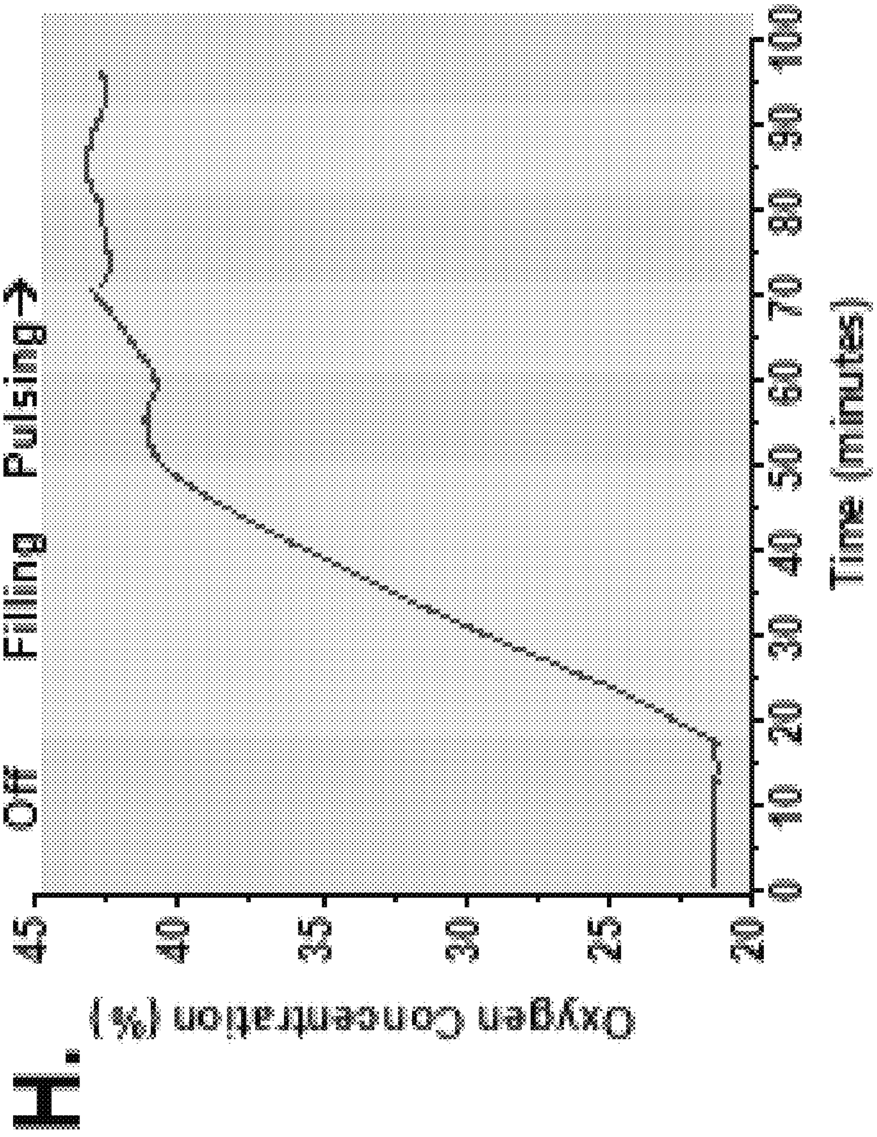

FIG. 7F is a plot illustrating pulsed mode operation of the bioelectronic device in FIG. 1A following an initial filling period, maintaining $O_2$ levels at about 45% at 50% duty cycle operation.

Figure 8A:
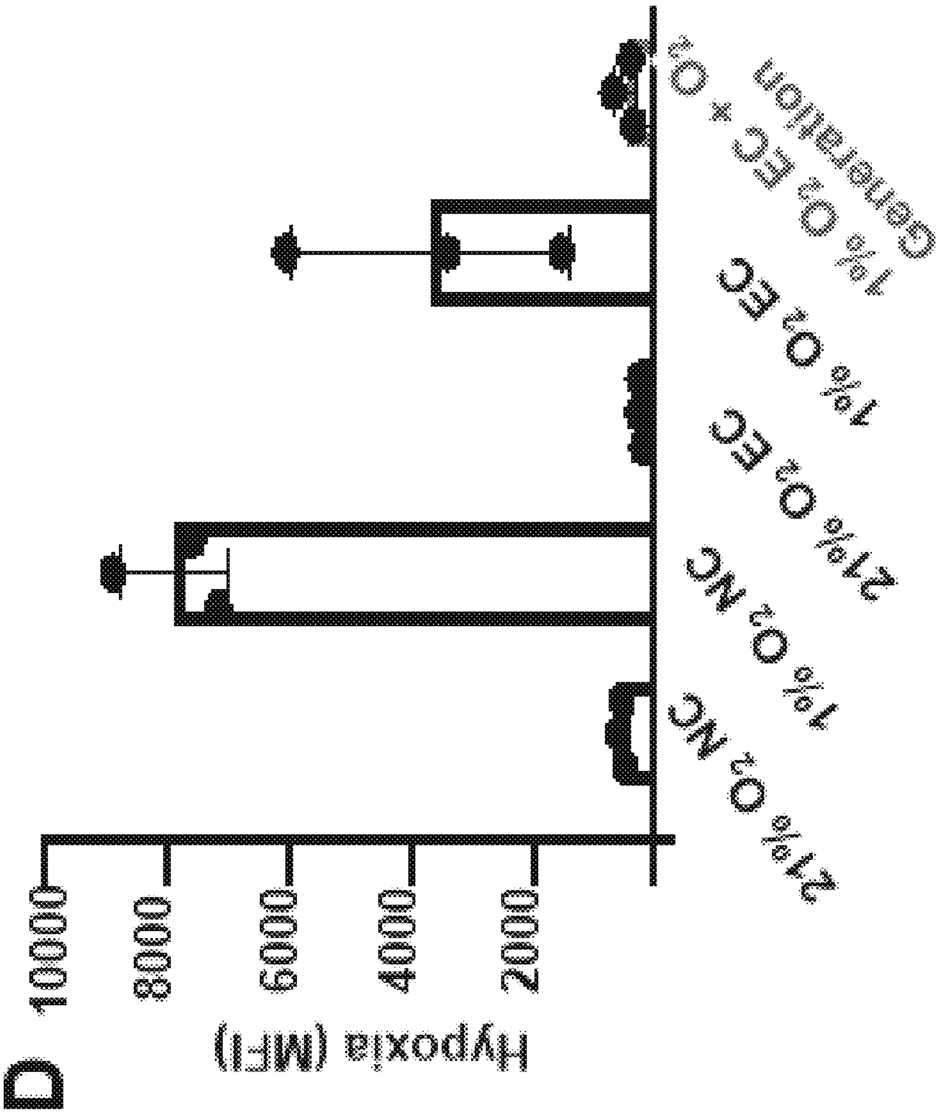

FIG. 8A is a plot illustrating mean fluorescence intensity (MFI) from HEK-293 cells after no encapsulation (NC) or encapsulation in the bioelectronic device in FIG. 1A (EC) for 12 hours in 1% $pO_2$ (hypoxic) with and without electrochemical $O_2$ generation and 21% $pO_2$ (normoxic) conditions for 24 hours (n=3 devices for all groups with error bars representing standard deviations).

Figure 8B:
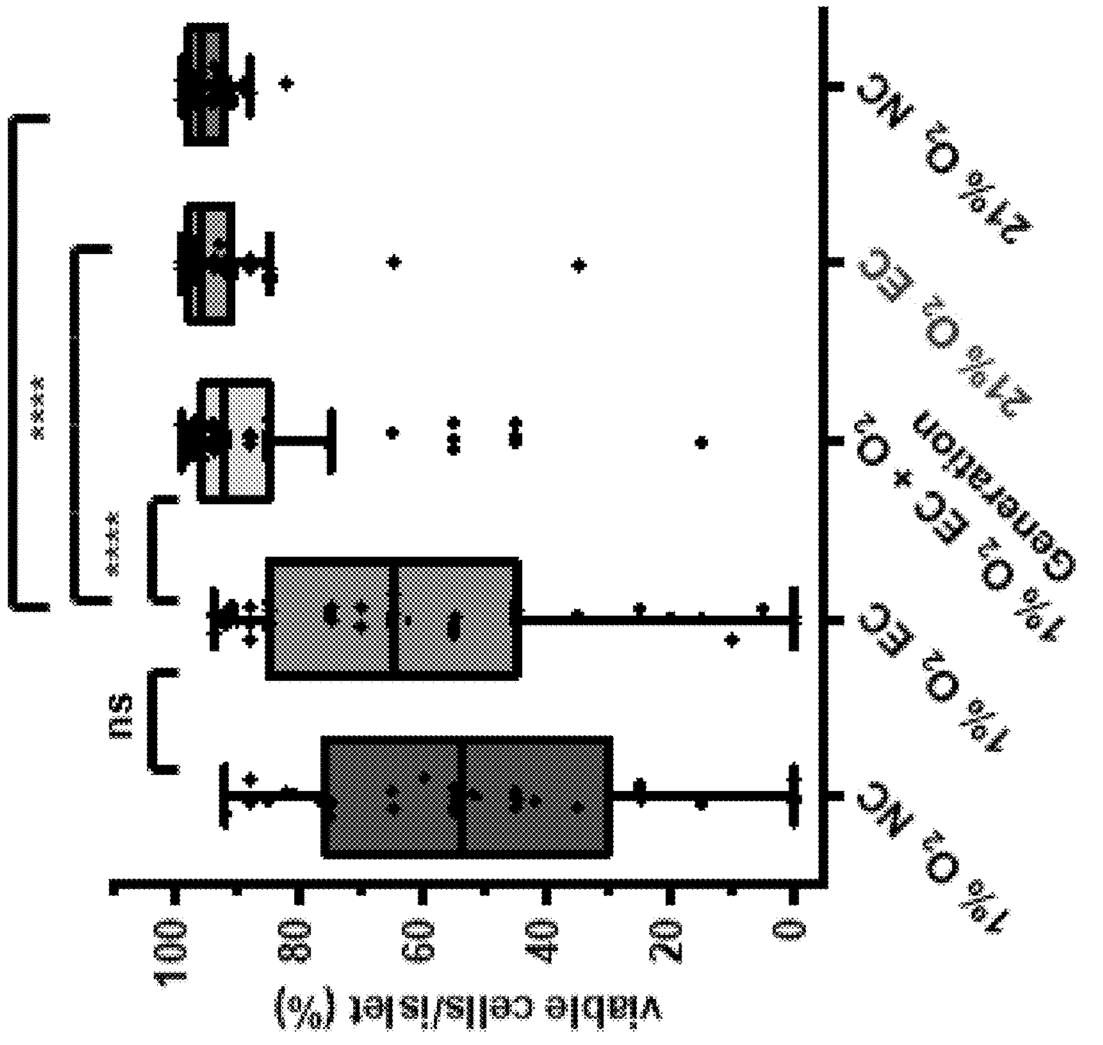

FIG. 8B is a plot illustrating flow-assisted cell sorting (FACS) measurements of rat islets after 72 hours under the same conditions as in FIG. 8A.

Figure 8C:
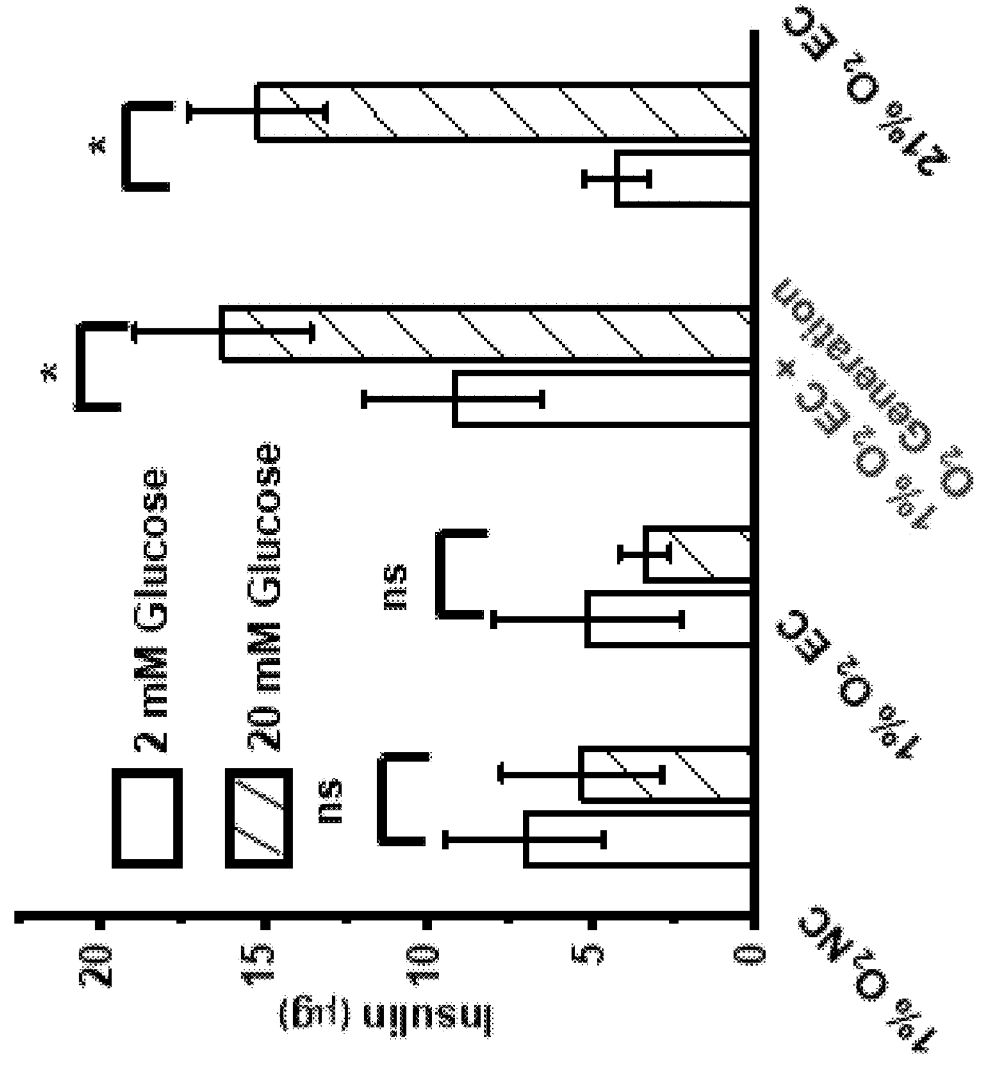

FIG. 8C is a plot illustrating glucose responsive insulin secretion (GSIS) at 2 glucose concentrations (2 mM, 20 mM) for encapsulated (EC) and naked (NC) rat islets after incubation in 1% $O_2$ for 72 hours with supplemental $O_2$ generation in one hypoxic group. (n=3, error bars represent standard deviations)

Figure 9:
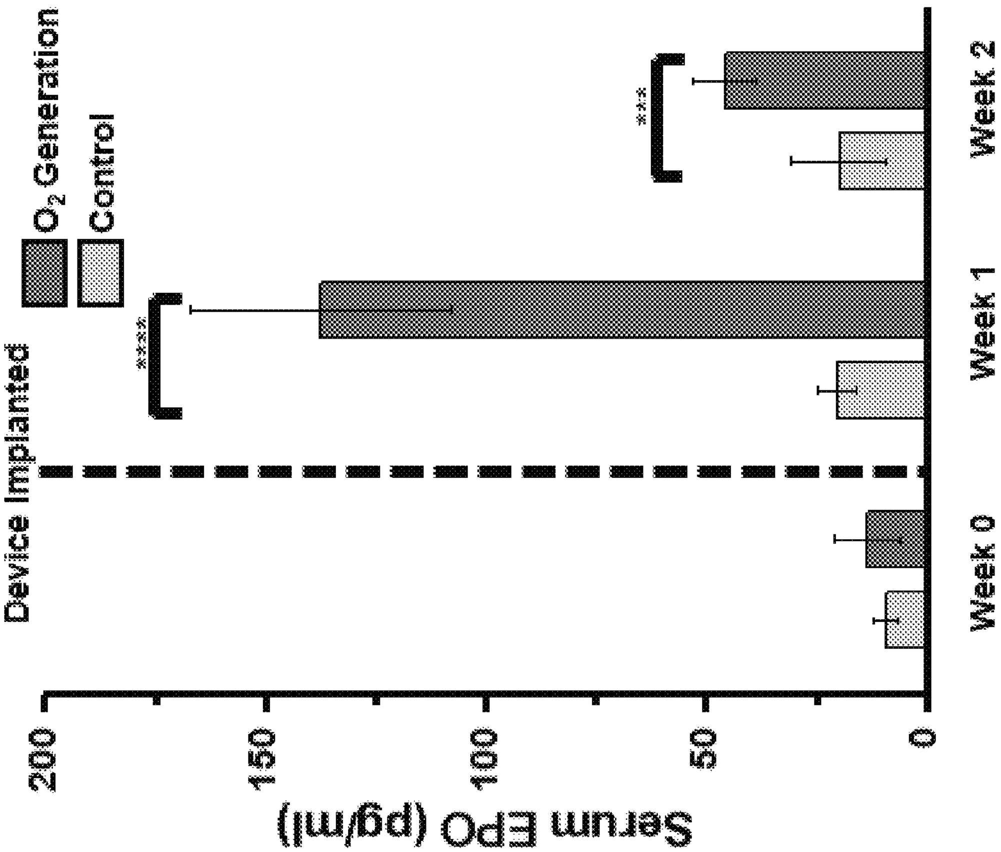

FIG. 9 is a plot illustrating serum erythropoietin (EPO) levels measured before and 2 weeks after transplantation of the bioelectronic device in FIG. 1A holding human embryonic kidney (HEK-293) cells modified to secrete EPO.

Figure 10A:
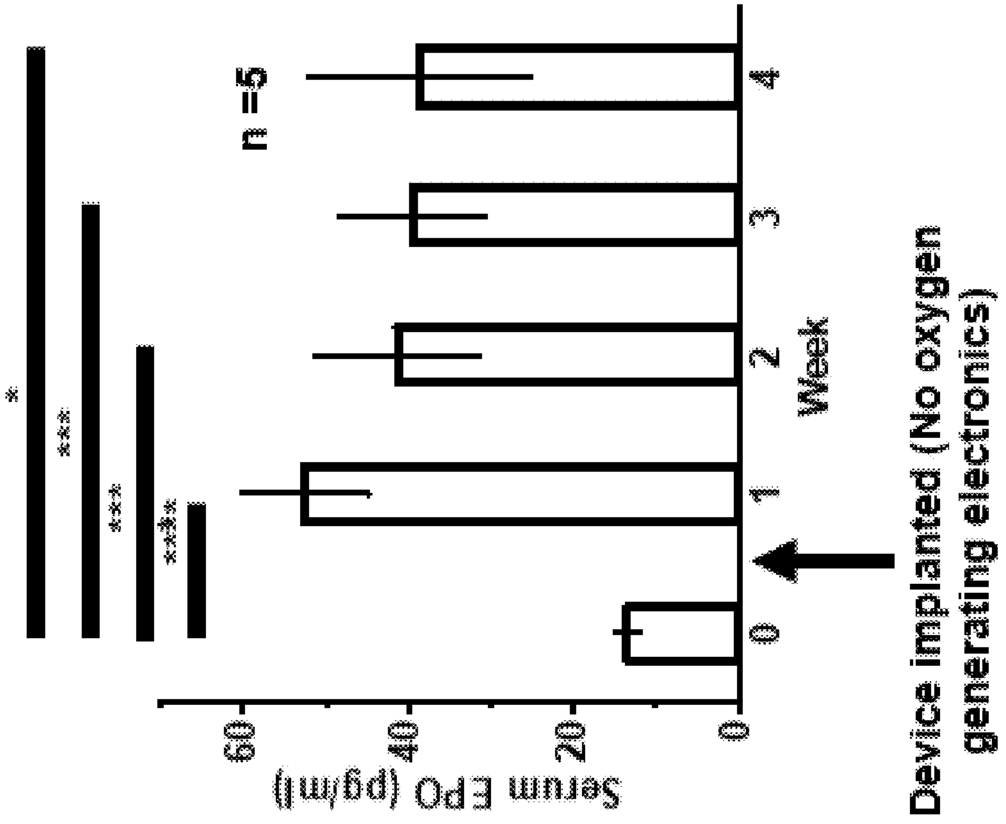

FIG. 10A is a plot illustrating serum EPO levels measured after implantation of the bioelectronic device in FIG. 1A holding human embryonic kidney (HEK-293) cells modified to secrete EPO and coated with an anti-fibrotic coating.

Figure 10B:
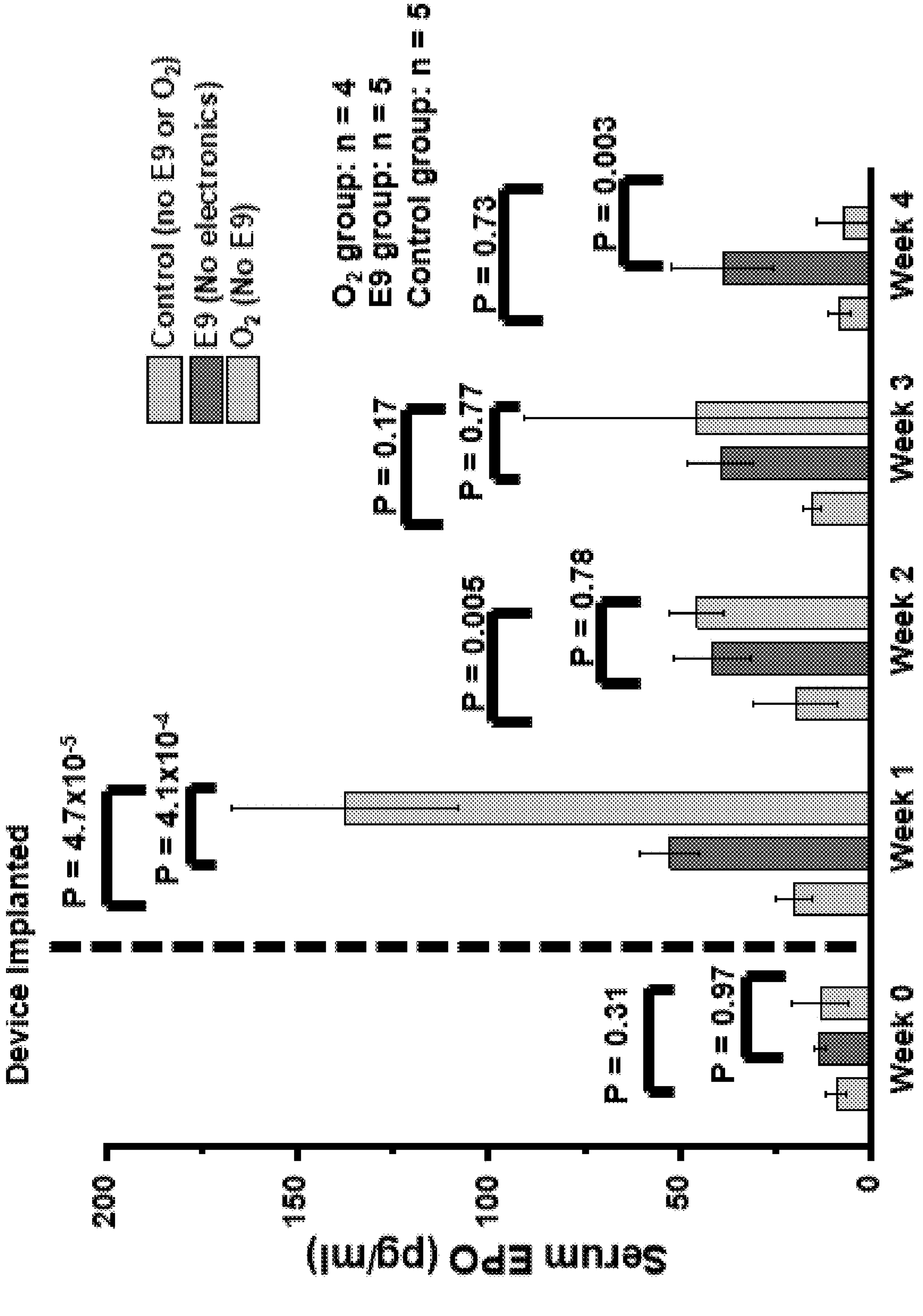

FIG. 10B is a plot comparing the data shown in FIG. 10A and FIG. 9.

DETAILED DESCRIPTION

Conventionally, therapeutic agents secreted by cells are administered via direct injection. A typical treatment regimen for a patient prescribed long-term administration of one of these therapeutic agents includes repeated painful injections, which can reduce adherence to the regimen.

Instead of using repeated direct injections, cell-based therapies can be used. Cell-based therapies use exogenous cells, either naturally secreting or engineered to secrete desired therapeutic agents, which are grafted or implanted into a host's body to administer the therapeutic agent to the host. This type of therapy can deliver a therapeutic agent to a patient over a long period of time and/or continuously. These cell-based therapies can be cost-effective therapies for several chronic disorders. However, these implanted therapeutic cells can be immunogenic to the host, resulting in the formation of fibrotic tissue around the cells and leading to high rates of hypoxia mediated cell death. Previous attempts using implanted cell-based therapies have relied on the host taking immune-suppressing medication (e.g., immunosuppressants) to reduce the formation of fibrotic tissue in order to increase the viability of the implanted therapeutic cells. However, these immune-suppressing medications increase the chances of infection, can have harmful side effects, and are not appropriate for all patients for a wide variety of reasons.

Two challenges to proper function of immune-isolating devices that physically separate implanted therapeutic cells from the host immune system use in vivo are: 1) foreign-body reactions (FBR) to the implanted device that can lead to fibrosis, causing cell death, and 2) an inadequate supply of oxygen to the therapeutic cells encapsulated in the device results in hypoxia-mediated cell death. The subcutaneous (SQ) locations in the host where a device may be more easily implanted and retrieved surgically have low oxygen levels and devices implanted in these regions are prone to fibrosis.

Fibrosis in particular has limited survival of immune-isolating devices implanted within hosts. Conventionally, these devices may have semi-permeable membranes that rely on passive diffusion of oxygen and nutrients, but the semi-permeable membranes have failed previously due to fibrosis. Fibrosis is a pathological wound healing mechanism in which extracellular matrix components including collagen build up. Extracellular components can block the semi-permeable membrane so that diffusion of oxygen and nutrients to the cells is limited or substantially stopped, resulting in cell death. For example, phase 1 trials with the PEC-Encap (Viacyte Inc.) device were paused due to fibrosis and poor engraftment.

In addition to fibrosis, immune-isolating devices have struggled to keep their therapeutic cells alive in oxygen deficient implantation sites. There have been several approaches to providing oxygen to grafted therapeutic cells implanted in a host to mitigate hypoxia-mediated cell death. One approach to mitigate cell death due to insufficient oxygen is to vascularize the device. Vascularization connects the host's vasculature with vasculature in the grafted cells so that the host's vasculature delivers oxygen to the graft. However, this approach has substantially failed to mitigate hypoxia-mediated cell death over long time scales. Prevascularization of the graft site prior to device implantation is another approach, but its outcome is unpredictable, includes multiple surgeries, and the host's immune system is usually suppressed to reduce the risk of cell death. Direct oxygen delivery to encapsulated therapeutic cells is another approach. Direct delivery has shown promise as a method to provide long-term graft viability, suggesting the importance of maintaining oxygen tension for cell survival. However, devices using direct delivery of oxygen typically have to have oxygen supplies refilled periodically (e.g., daily via a cutaneous port), making this approach clinically undesirable. Fibrosis continues to be a problem with this technique.

A well-oxygenated, subcutaneous implant with limited fibrosis provides long term survival and function of protein-secreting therapeutic cells in vivo. Encapsulating the therapeutic cells within a chamber can increase the length of survival after implantation. The chamber includes a semi-permeable, immune-isolation membrane that acts as a pathway for the diffusion of oxygen and nutrients to the cells from the host and delivery of the therapeutic protein from the cells to the host.

Accordingly, aspects disclosed herein are directed to implantable bioelectronic device(s) (also sometimes referred to macrodevices) that encapsulate biological entities (e.g., primary human cells, stem cell derived cells, cell lines, xenogeneic cells, or other therapeutic cells) to shield them from immunogenic effects in the body in order to increase their long-term survival without the use of immune-suppressing medication. The bioelectronic device generates its own oxygen supply to create an oxygen-rich microenvironment for the cells and prevents immunogenic attack by physically isolating the therapeutic cells from the host's immune system. The bioelectronic device does not need an external oxygen source (e.g., direct oxygen supplied periodically via a cutaneous port) to keep the cells viable. The bioelectronic device includes a semi-permeable immune-isolation membrane that simultaneously provides a conduit for the delivery of therapeutic agents secreted by the therapeutic cells to the host and provides the cells access to nutrients from the host. In some embodiments, the bioelectronic device includes an anti-fibrotic coating on its outer surface and/or on its semi-permeable immune-isolation membrane to suppress fibrotic tissue formation on the bioelectronic device which might otherwise suppress or prevent the delivery of the therapeutic agent from the cells to the host and the cells' access to the host's nutrients.

FIG. 1A shows a cross-sectional view of an example of a bioelectronic device 100. The bioelectronic device 100 is small enough to be implanted into a host's body and later retrieved. For example, the device 100 may have a volume of about 1 $cm^3$ to about 500 $cm^3$, including all values and sub-ranges in between, when the device 100 is intended for implantation in a human. As another example, the device 100 may have dimensions of up to 10 cm by 10 cm by 5 cm. The device 100 may have any suitable shape such as, for example, a flat, sheet-like shape. The flat, sheet-like shape may provide the ability for the device 100 to fold in on itself or to fold around an organ. In other examples, the device 100 has a rectangular shape, an oval shape, a circular shape, or a rectangular shape with rounded edges. In another example, the device 100 can be flexible with a, long, cylindrical shape.

The bioelectronic device 100 includes an electrochemical cell 113 to generate oxygen that includes a cation-conducting membrane 112, electrodes 114*a* and 114*b* on either side of the membrane 112. The electrochemical cell 113 is coupled to/supported by (e.g., mounted onto or into) a substrate 110, upon which a power source 118 and a light source 116 (e.g., a light emitting diode, LED) are disposed. The membrane 112 may be disposed in a cavity 115 in the substrate 110. The cavity 115 may be a hole formed through the thickness of the substrate 110. The power source 118 provides power to the light source 116 and to electrochemical cell's electrodes 114*a* and 114*b* for the generation of oxygen via water electrolysis (also called water splitting). The power source 118 may include a battery and/or capacitor that is powered wirelessly or via wired coupling, as described in more detail below. The light source 116 is an optional component that may provide light stimulus to the therapeutic cells encapsulated in the device 100 to stimulate and/or regulate their production of therapeutic agents. The device 100 also includes a gas diffusion chamber 122 in which oxygen generated by the electrochemical cell 113 is stored, and a cell housing chamber 124 (also sometimes referred to as a cell reservoir) in which the therapeutic cells are encapsulated. The device 100 includes a housing 120 that surrounds and protects the other components. One side of the device adjacent to or forming part of the cell housing chamber 124 may include a semi-permeable immune-isolation membrane 126 for the transport of oxygen and nutrients to the cells from the host and for the transport of therapeutic agents from the cells to the host. The immune-isolation membrane 126 can be configured to exclude immune cells (e.g., small lymphocytes having a size of about 5 μm to about 10 μm).

Figure 1B:
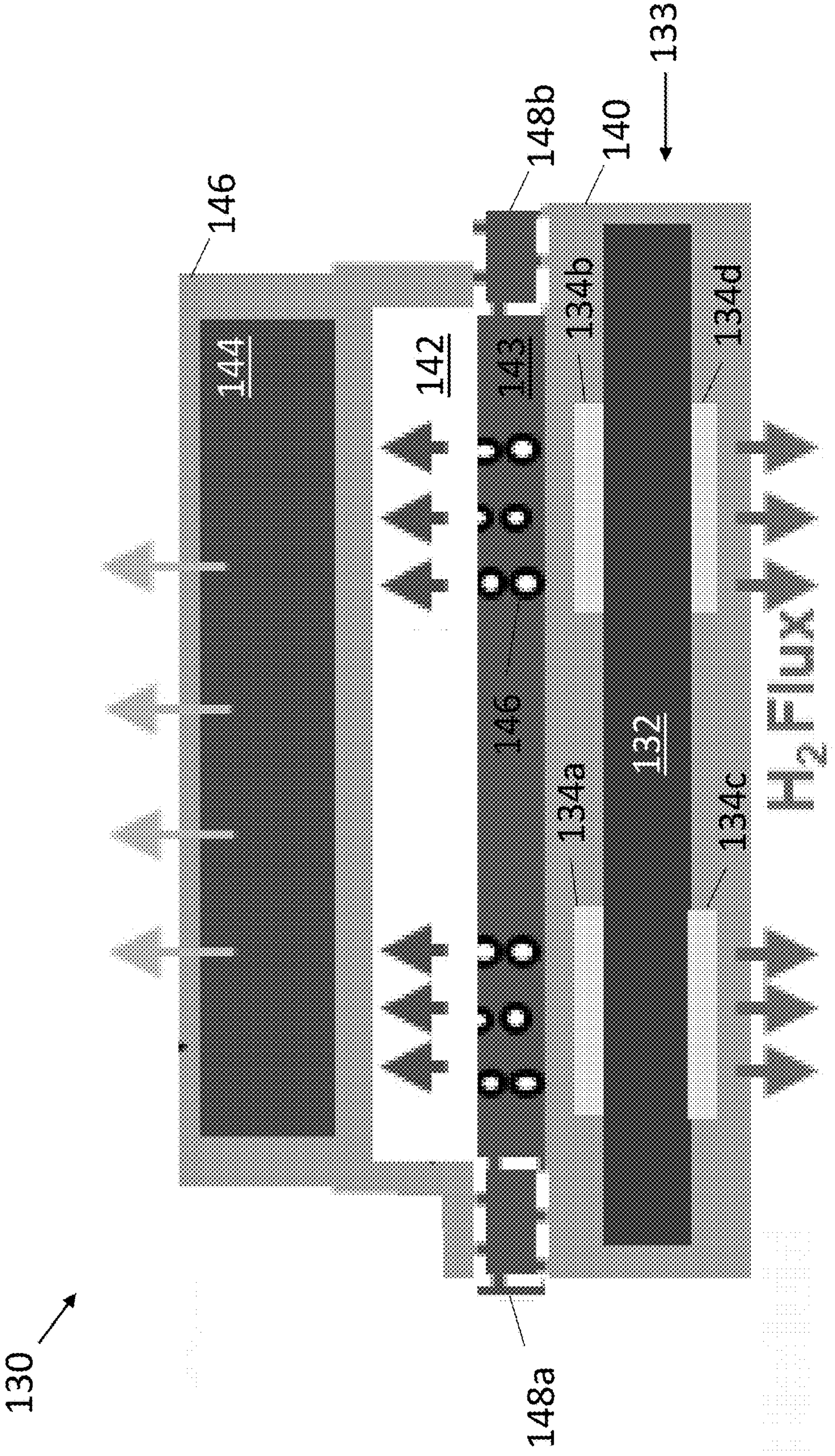
FIG. 1B illustrates a cross-sectional view of another bioelectronic device for encapsulated cell therapies.

FIG. 1B shows a cross-sectional view of another bioelectronic device 130. The device 130 includes an electrochemical cell 133 with two sets of electrodes 134*a*-134*d*, with pairs of electrodes disposed directly across from each other on either side of a single cation-conducting membrane 132. The gas diffusion chamber 142 holds oxygen gas generated by the electrochemical cell 133 and water 143 (e.g., deionized water) used as the reactant in the electrochemical water electrolysis reaction that generates oxygen gas. The water 143 can be added to the chamber 142 via one of the two ports 148*a* and 148*b* into the gas diffusion chamber 142. The ports 148*a* and 148*b* may be small openings in the sidewalls of the device 130. The ports 148*a* and 148*b* may be formed via soft lithography during device molding used to form the device 130 or the ports 148*a* and 148*b* may be formed by cutting holes in the sidewalls of the device 130 after it has been formed. The ports 148*a* and 148*b* may be used to periodically replenish the water 143 as the electrochemical cell 133 depletes the water 143 if desired (e.g., with water from biological fluid in the interstitial space in which the device 130 is implanted). Having two ports may be preferred so that as water or fluid flows into the gas diffusion chamber 142 through one port, the water or fluid flowing in can displace existing gases or fluids in the gas diffusion chamber 142, which can flow out of the gas diffusion chamber 142 through the other port. In another version, the device 130 does not include any ports and the gas diffusion chamber 142 is replenished via pervaporation of water through the device's housing.

The cell housing chamber 144 houses the therapeutic cells and receives oxygen generated by the electrochemical cell 133 via the gas diffusion chamber 142. A side of the cell housing chamber 144 includes the semi-permeable immune-isolation membrane 146 that transports oxygen, nutrients, and therapeutic agents. The device 130 is encapsulated in a housing 140.

Figure 1C:
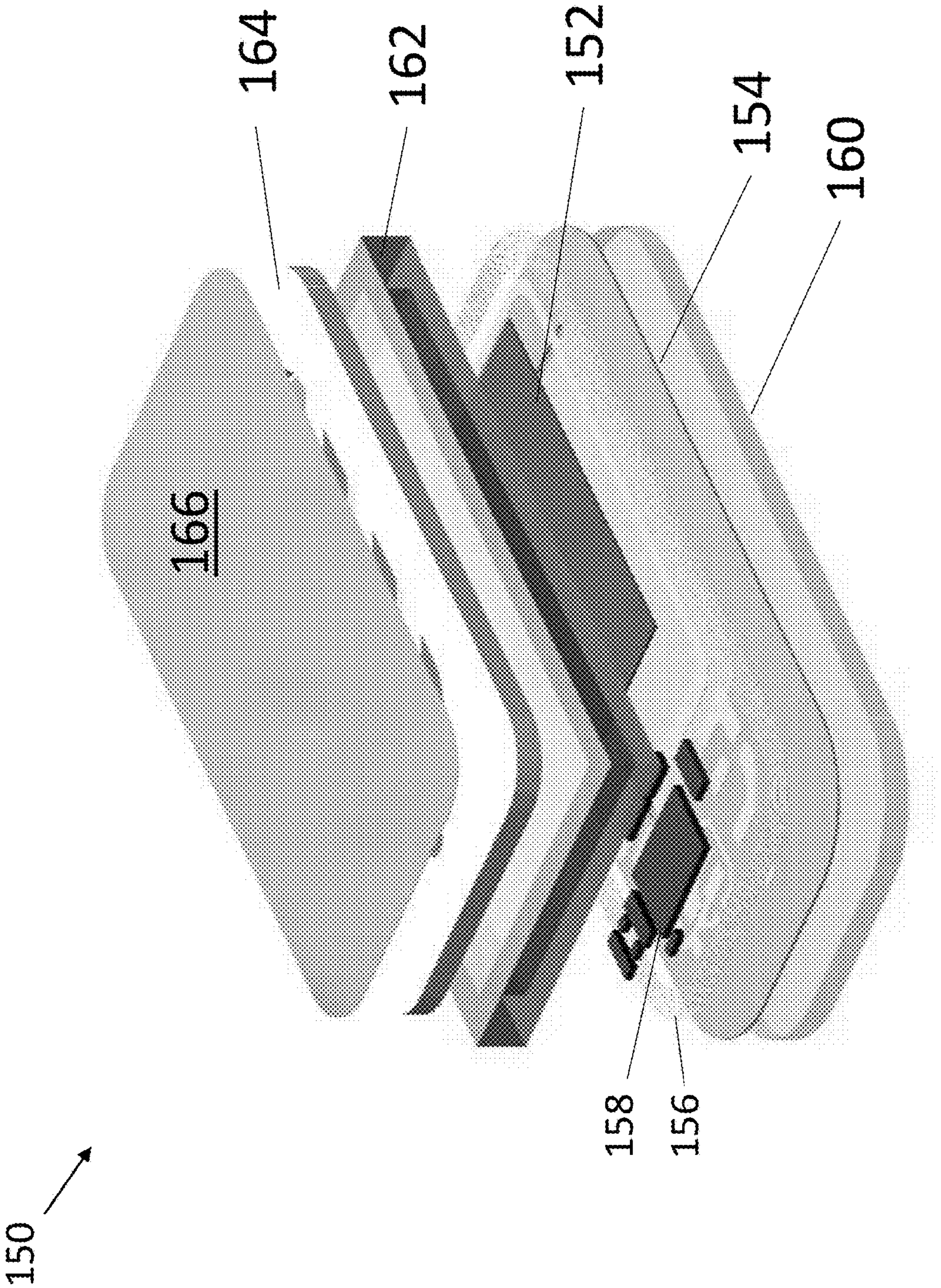
FIG. 1C illustrates an exploded perspective view of a bioelectronic device for encapsulated cell therapies.
Figure 1D:
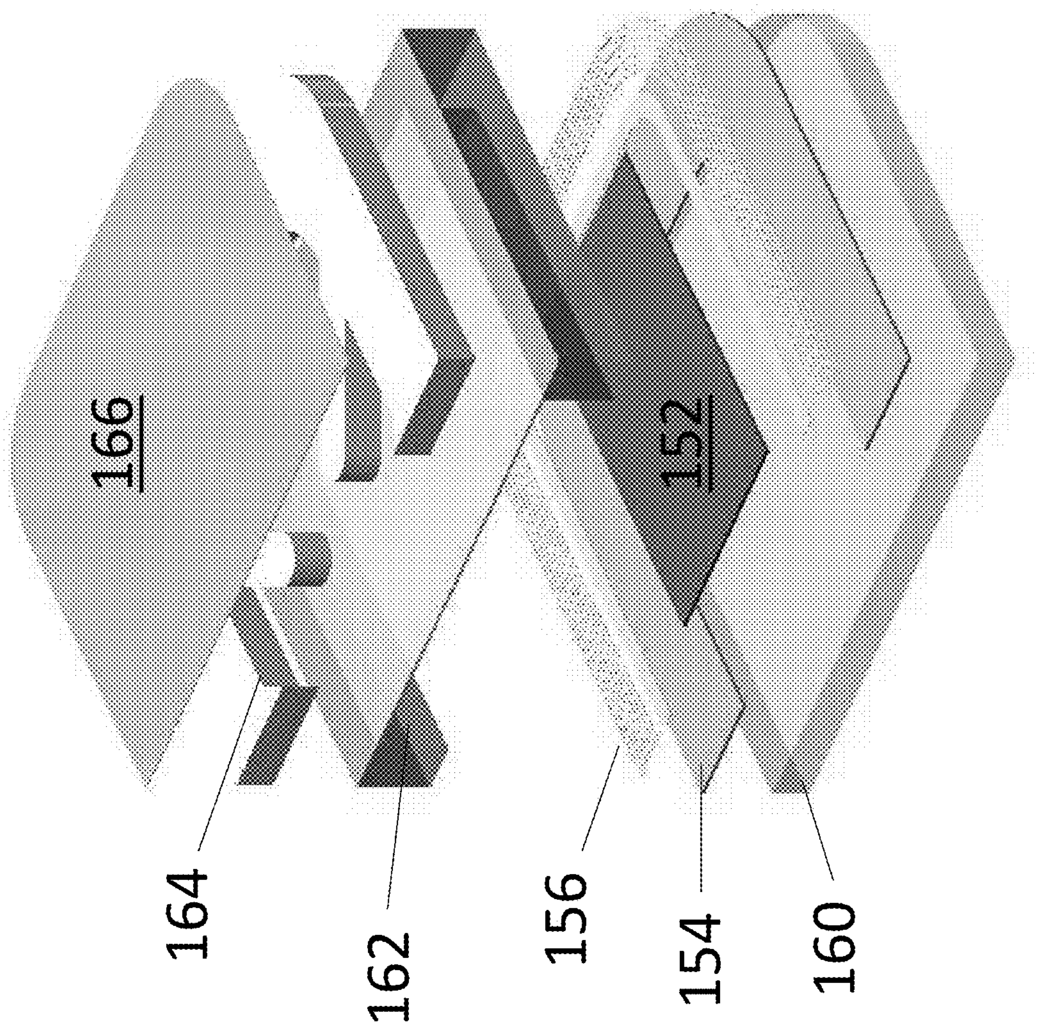
FIG. 1D illustrates a cross-sectional exploded perspective view of the bioelectronic device in FIG. 1C.

FIG. 1C shows an exploded perspective view of another bioelectronic device 150. FIG. 1D shows a cross-sectional view of the device 150 shown in FIG. 1C. The bioelectronic device 150 includes an electrochemical cell 133 with a cation-conducting membrane 152 embedded in a board 154 and at least one pair of electrodes (not shown) on either side of the membrane 152 to generate oxygen. A power supply 158 and an inductor 156, part of a wireless receiver circuit (also called a wireless power harvesting system) disposed on the board 154, provide wireless operation of the device 150, as described in more detail below. The board 154 is disposed on a substrate 160 that is a low-modulus silicone elastomer (e.g., polydimethylsiloxane) that is soft, flexible, and biocompatible. The device 150 also includes a gas diffusion chamber 162 receiving and storing oxygen gas generated by the electrochemical cell. A cell housing chamber 164 stacked on top of the gas diffusion chamber 162 houses therapeutic cells and receives oxygen gas from the gas diffusion chamber 162. The semi-permeable immune-isolation membrane 166 disposed on one side of the cell housing chamber 164 transports oxygen, nutrients, and therapeutic agents.

Example Device

The following description is explained with respect to the device of FIG. 1A for ease of understanding but may apply to any embodiment of the device. The housing 120 encapsulates the components in the bioelectronic device 100, including the electrical and electrochemical components to prevent fouling and shorting of these components in the host's biological fluid. The housing material is biocompatible and impermeable to liquid water. The housing 120 may or may not be permeable to water vapor. The housing 120 also prevents the intrusion of ions commonly found in biological fluids (e.g., $Na^+$, $K^+$, and $Cl^-$) that can be involved in parasitic side reactions that can produce potentially harmful species like $Cl_2$ gas in the one or more electrochemical cells 113 used to generate oxygen for the bioelectronic device 100.

In one embodiment, the housing 120 is a low-modulus (e.g., having a Young's modulus of about 50 kPa to about 5 MPa, including all values and sub-ranges in between) silicone elastomer (e.g., polydimethylsiloxane) that is soft, flexible and biocompatible. The housing 120 may have a flexural rigidity (also known as bending stiffness) between $10^{-5}$N-m and $10^{-11}$ N-m, including all values and sub-ranges in between. The housing 120 may have a thickness of about 20 μm to about 2 mm, including all values and sub-ranges in between. The silicone elastomer has a high permeability to $O_2$, $H_2O$ and $H_2$, allowing for efficient transport of reactants and products to the one or more electrochemical cells. Water permeates through silicone via the process of pervaporation (a combination of permeation and evaporation) that substantially excludes solvated salt ions. Because the silicone substantially excludes salt ions, the water inside the device is not conductive enough to create a risk of electrical shorting. In another embodiment, the housing 120 is a microporous parylene, a microporous polyimide, and/or a microporous polyisobutylene, where the micropores facilitate transport of $H_2O$, $O_2$, and $H_2$ and the material itself is not permeable to these species.

The bioelectronic device 100 includes an electrochemical cell 113 that generates oxygen. In one example, the main electrochemical reaction for generating oxygen is water splitting and the cation-conducting membrane 112 is a proton exchange membrane (PEM). The cation-conducting membrane 112 may have a size that is about 20% to about 100% of the area of the device. For example, the cation-conducting membrane 112 may have a size of about 1 cm by 1 cm to about 10 cm by 10 cm, including all values and sub-ranges in between. The thickness of the cation-conducting membrane is about 1 mm to about 2 mm. The cation-conducting membrane 112 preferentially transports hydrogen ions (protons) in a highly specific manner. As an example, a PEM proton-conducting membrane is comprised of a fluoropolymer and is an ionomer with extremely high proton conductivities (e.g., ~0.1 S/cm) based on a combination of favorable chemistry (e.g., presence of sulfonic acid groups) and morphology (e.g., presence of pores). The PEM may be a commercially available membrane (e.g., Nafion™) having perfluorinated backbones similar to those of existing clinically approved biomaterials (e.g., polytetrafluoroethylene, PTFE).

The electrochemical cell 113 also includes at least one pair of electrodes 114*a* and 114*b* disposed on opposite sides of the cation-conducting membrane 112. The electrodes 114*a* and 114*b* are made of biocompatible materials such as, for example, thin carbon (e.g., graphite sheets/graphene), inert metals (e.g., gold, iridium, or platinum), an anode catalyst (e.g., iridium-ruthenium oxide), combinations thereof, and/or the like. The electrodes 114*a* and 114*b* may be attached to the cation-conducting membrane 112 via conductive epoxy so that the electrical interfaces between the electrodes 114*a* and 114*b* and the membrane 112 provide low-impedance charge injection. Alternatively, the electrodes 114*a* and 114*b* may be deposited on the membrane 112 via thin film evaporation or sputtering deposition. Alternatively, the cation-conducting membrane 112 may be soldered to electrodes 114*a* and 114*b* at interfaces. Alternatively, the electrodes 114*a* and 114*b* and cation-conducting membrane 112 may be held together using mechanical compression from the housing 120.

The electrochemical cell 113 is mounted onto or within a flexible substrate 110. The substrate 110 may be a flexible printed circuit board (PCB) upon which electronic components are disposed and electrically coupled. All of the electrical components can be selected to operate at low power (e.g., less than 100 mW). The flexible substrate 110 may be constructed from high-quality rolled metal structured into an inert polymeric substrate (e.g., polyimide). The substrate 110 may have a thickness of about 80 μm to about 150 μm (e.g., 120 μm), including all values and sub-ranges in between, so that the substrate 110 is flexible (e.g., having a flexural rigidity of about $10^{-4}$ N-m and $10^{-8}$ N-m. Surface-mounted electronic components are mounted onto the board via reflow soldering. The layout of the PCB can be easily modified to support a range of ultraminiaturized, commercially available electronic components (e.g., for wireless power harvesting, rectification, and power management and control) without a significant increase in overall device footprint.

The electrochemical cell 113 splits water via electrolysis into hydrogen and oxygen ($2H_2O \rightarrow 2H_2 + O_2$) when a voltage is applied to the electrodes 114*a* and 114*b*. The applied voltage is 1.23 V (the thermodynamic water-splitting voltage) to about 2 V, including all values and sub-ranges in between. The half reactions at the anode 114*b* and cathode 114*a*, respectively, are $2H_2O \rightarrow 4H^+ + O_2 + 4e^-$ (anode) and $4H^+ + 4e^- \rightarrow 2H_2$ (cathode). The water reacting at the anode 114*b* may be water vapor or liquid water. The electrochemical cell 113 preferentially transports protons ($H^+$ ions) generated at the anode **114*b* to the cathode 114*a* through the cation-conducting membrane 112. The electrochemical cell 113 does not require liquid electrolytes with ionic salts. $H_2$ is produced at a low rate of about 10 nmol/second (or roughly 1 mL/hour) and is quickly dispersed away from the device 100** because of its solubility in blood. Additionally, $H_2$ exposure is non-toxic to cells and does not affect device performance.

The current (I) generated by the electrochemical cell 113 when the applied voltage is greater than 1.23 V is linearly proportional to the $O_2$ generation rate. Increasing applied voltage between 1.23 V and 2 V results in increasing current and $O_2$ generation rates. The current generated by the electrochemical cell when a voltage greater than 1.23 V is applied at the electrodes is given by: I=nFM, where I is the total current, n is the number of electrons for a single molecule of oxygen (n=4), F is Faraday's constant (F=96, 500 C/mole) and M is the molar generation rate of oxygen. In this way, oxygen production can be directly modulated by current through the electrode stack. The electrochemical cell 113 uses currents of about 1 mA to about 10 mA (e.g., 1 mA, 2 mA, 3 mA, 4 mA, 5 mA, 6 mA, 7 mA, 8 mA, 9 mA, or 10 mA), including all values and sub-ranges in between, correspond to oxygen generation rates (OGR) of about 1 nmol/s to about 30 nmol/s (e.g. 1 nmol/s, 5 nmol/s, 10 nmol/s, 15 nmol/s, 20 nmol/s, 25 nmol/s, or 30 nmol/s), including all values and sub-ranges in between. Using the metabolic consumption rate of oxygen in human cells, which is about 10 amol/cell/s to about 50 amol/cell/s, this oxygen generation rate is sufficient to support about 5 million to about 80 million cells with a 10% operational capacity (e.g., a cycling frequency of about $1.6\times10^{-5}$ Hz (i.e., cycling once per day) to about 1 Hz (i.e., cycling once per second); and a duty cycle of about 4% to about 50%). As an example, the oxygen generating electrochemical cell 113 can rapidly (e.g., in less than 20 minutes) increase $O_2$ levels from less than 2% to greater than 45% while maintaining low current (e.g., less than 4 mA) operation. In this way, the device 100 provides an adequate supply of oxygen to encapsulated cells to prevent hypoxia mediated cell death.

The cation-conducting membrane 112 may be disposed in a water-permeable silicone housing 120. Water may reach the surface of the cation-conducting membrane 112 through a process of pervaporation wherein water first evaporates and dissolves into the silicone polymer through a first surface and then diffuses through the polymer and evaporates out through a second surface that is directly contacting the cation-conducting membrane 112. Once water reaches the cation-conducting membrane surface, the resulting reaction can be broken down into anodic and cathodic half reactions described above. The electrochemical current is given be I=NFM, where I is the current, N is the number of electrons to create a single molecule of oxygen (N=4), F is Faraday's constant (96,500 A-s), and M is the molar oxygen generation rate. Accordingly, M is given by M=INF and is directly proportional to the electrochemical current.

The water used as fuel for the electrochemical reaction generating oxygen may be pure water, water vapor, and/or water from extracellular fluid. As an example, pure water may be added to the electrochemical cell 113 before it is sealed within the housing 120. In this way, the electrochemical cell 113 has an immediate water source for the water splitting reaction once implanted. As another example, the housing 120 may include one or more ports (e.g., ports **148*a* and 148*b* in FIG. 1B) that act as conduits for adding water to the gas diffusion chamber 122 in the assembled device 100, initially before implantation and/or periodically while implanted. As another example, the assembled device 100 may be hydrated prior to implantation by placing the assembled device 100 in a warm humid environment (e.g., in a water bath at a temperature of 75° C.) so that water vapor diffuses through the housing material into the device. As another example, once the device 100 is implanted, the housing material may transport water vapor from the host's extracellular fluid via pervaporation while inhibiting the transport of extracellular fluid species (e.g., $Cl^-$ or $Na^+$) that could facilitate toxic side reactions. One or several of these example methods may be used to hydrate the device 100**.

The bioelectronic device 100 also includes a gas diffusion chamber 122. The gas diffusion chamber 122 acts as a storage chamber for $O_2$ gas generated by the electrochemical cell. Oxygen generated at the electrochemical cell 113 diffuses through a layer of the housing 120 (e.g., made of PDMS) between the electrochemical cell 113 and the gas diffusion chamber 122, and then diffuses through a second layer of the housing 120 between the gas diffusion chamber 122 and the cell housing chamber 124. The gas diffusion chamber 122 may have a volume of about 0.5 $cm^3$ to about 100 $cm^3$, depending on the number of cells encapsulated in the device 100. For example, the gas diffusion chamber 122 may have a size of about 1 cm by about 1 cm by about 0.5 cm or a size of about 10 cm by about 10 cm by about 1 cm, or any value or sub-ranges in between. As an example, during electrochemical cell 113 operation, the gas diffusion chamber 122 may have a locally rich $O_2$ environment (e.g., about 10% to about 50% $O_2$ or about 30 kilopascals to about 50 kilopascals of oxygen partial pressure). The gas diffusion chamber 122 is disposed adjacent to or directly in contact with the anode **114*b* of the electrochemical cell 113. The gas diffusion chamber 122 may be bonded to the electrochemical cell 113 using simple condensation reactions between the chamber 122 and the electrochemical cell 113** by UV-functionalizing or oxygen-plasma-functionalizing surfaces of both components, disposing one on the other, and then exposing them to UV light or oxygen-rich plasma. The addition of energy to the surface of the components, in the form of an oxygen-rich plasma or direct exposure to high energy UV light breaks Si—O bonds on the silicone surface and creates hydrophilic—OH groups. The —OH groups can then bond with OH groups on the second functionalized silicone surface, where the OH—OH groups condense to form Si—O—Si (two bonded surfaces) and water (a by-product).

The gas diffusion chamber 122 is constructed of biocompatible flexible polymer that is permeable to oxygen gas. For example, the gas diffusion chamber 122 may be made of silicone elastomer, polyurethane, biocompatible epoxy, or a combination thereof. Preferably, the gas diffusion chamber 122 is made of silicone. The gas diffusion chamber 122 may be enclosed on all sides and oxygen gas may diffuse into and out of the chamber 122 through its walls. The thickness of the walls of the chamber 122 can be varied to change the oxygen transport rate across chamber wall, with thicker walls having lower transport rates. As an example, the thickness of the walls of the chamber 122 may be about 50 μm to about 2 mm, including all values and sub-ranges in between. The sidewalls of the gas diffusion chamber 122 may be much thicker (e.g., at least 500 μm thicker) than the top and bottom layers of housing material between the gas diffusion chamber 122 and the cell housing chamber 124 and the electrochemical cell 113, respectively, so that oxygen gas diffuses at a faster rate between the electrochemical cell 113, the gas diffusion chamber 122, and the cell housing chamber 124 than the rate of diffusion of oxygen gas out of the device through the device's sidewalls. The sidewalls may also have a smaller surface area than the layers between the components to preferentially direct oxygen gas diffusion through the components.

The filling rate of the gas diffusion chamber 122 can depend directly on the electrochemical current, the size of the gas diffusion chamber 122, and the thickness of the chamber's walls. Emptying rates depend on diffusive $O_2$ loss through chamber walls and consumption of $O_2$ by the therapeutic cells. Preferably, during operation of the electrochemical cell 113, the filling rate of the chamber is about 8 to about 9 times faster than its emptying rate, allowing for $O_2$ storage for extended periods (e.g., 6-8 hours) without the need for constant operation of the electrochemical cell 113.

The bioelectronic device 100 also includes a cell housing chamber 124 in which the therapeutic cells are encapsulated. The dimensions of the cell housing chamber 124 may be similar to those of the gas diffusion chamber 122. The cell housing chamber 124 houses therapeutic cells with a packing density of about 0.5 million cells per $cm^2$ to about 10 million cells per $cm^2$. The cell housing chamber is disposed on a side of the gas diffusion chamber 122 opposite the side facing the anode 114*b*. In an example, the cell housing chamber 124 and the gas diffusion chamber 122 share a wall so that the cell housing chamber 124 is stacked directly on top of the gas diffusion chamber 122. The shared wall may be a biocompatible polymer (e.g., silicone elastomer, polyurethane, biocompatible epoxy, or a combination thereof) with a fixed thickness to mediate diffusive oxygen gas transport at a constant and uniform rate from the gas diffusion chamber to the cell housing chamber. The thickness of this wall may be about 10 μm to about 500 μm (e.g., 10 μm, 25 μm, 50 μm, 75 μm, 100 μm, 150 μm, 200 μm, or 500 μm), including all values and sub-ranges in between. The side walls (as in, the walls other than the wall facing the gas diffusion chamber and the wall opposite the wall facing the gas diffusion chamber) of the cell housing chamber 124 may be constructed of the same or similar biocompatible polymer as the shared wall and may have a larger thickness than the other walls to prevent oxygen diffusion out of the sides of the device. The wall of the cell housing chamber 124 opposite the wall facing the gas diffusion chamber 122 includes a porous immune-isolation membrane 126.

The cell housing chamber 124 can house many different types of therapeutic cells and varying amounts of cells to provide different types of treatments. For example, the cell housing chamber 124 can house about 1 million to about 1 billion cells (e.g., 2 million, 5 million, 10 million, 20 million, 30 million, 50 million, or 1 billion), including all values and sub-ranges in between. The bioelectronic device 100 can keep these cells alive and functioning inside of a host for a period of about 1 month to about 10 years (e.g., 1 month, 2 months, 3 months, 6 months, 12 months, 2 years, 5 years, or 10 years).

The porous immune-isolation membrane 126 separates the cells from the host's immune system while facilitating gas and nutrient transport into and out of the cell housing chamber 124. The membrane 126 is adhered to the cell housing chamber 124 using chemical bonding and/or an adhesive (e.g., PDMS-PDMS bonding or silicone-based adhesives). The membrane 126 is made of a biocompatible material and includes a plurality of pores. The membrane 126 has a thickness of 6 μm to about 30 μm, and preferably about 20 μm, for ease of handling. The membrane 126 has a high transport rate for the transport of oxygen and nutrients while blocking the entry of harmful immune elements from the host. The membrane's transport rate is dependent on the membrane's material and pore structure. The membrane 126 excludes cells from the host, including immune cells (e.g., granulocytes, lymphocytes, and macrophages) and other cells (e.g., red blood cells and platelets), using size filtering through pores in the membrane 126.

In one embodiment, the immune-isolation membrane 126 is made of silicone elastomer (e.g., PDMS) and has an ordered and uniform pore structure to provide a uniform high transport rate across the entire surface of the membrane 126. The ordered and uniform pore structure includes pores distributed in a grid (e.g., a simple cubic, face-centered cubic, body-centered cubic, or hexagonal grid pattern), with regular spacing and sizing between pores. The silicone elastomer PDMS has a high diffusivity to $O_2$ of about $0.5\times10^{-5}$ $cm^2/s$ to about $5\times10^{-5}$ $cm^2/s$, and preferably at least $3.5\times10^{-5}$ $cm^2/s$, comparable to that of liquid water ($2.3\times10^{-5}$ $cm^2/s$). With this high diffusivity, oxygen transport can occur through the entire surface of the membrane made of PDMS. Because of the membrane's high diffusivity to $O_2$, $O_2$ flux into and out of the cell housing chamber scales linearly with diffusivity (Fick's Law). The pores in the membrane 126 have a diameter of about 20 nm to about 5 μm (e.g., 20 nm, 50 nm, 100 nm, 200 nm, 500 nm, 800 nm, 1 μm, 2 μm, 3 μm, 4 μm, or 5 μm), including all values and sub-ranges in between, to prevent the ingress of harmful immune elements from the host into the cell housing chamber 124. As an example, the pores in the membrane 126 may have a diameter of about 400 nm to about 1 μm. The size of the pores is selected to exclude cells while not excluding molecules (e.g., therapeutic agents). The pores in the membrane 126 have a cross-sectional area of about 314 $nm^2$ to about 20 $μm^2$ (e.g., 314 $nm^2$, 350 $nm^2$, 400 $nm^2$, 500 $nm^2$, 1 $μm^2$, 2 $μm^2$, 5 $μm^2$, 10 $μm^2$, or 20 $μm^2$), including all values and sub-ranges in between. The total open area in the membrane 126 is about 0.5% to about 20%, including all values and sub-ranges in between.

Conventionally, creating a PDMS immune-isolation membrane with an ordered and uniform pore structure with a pore size of 1 μm or less was challenging. Conventional approaches based on demolding from post structures have been used to form pores in the 10 μm range in PDMS, but these approaches have not successfully formed pores in PDMS in the submicron range. The challenge is related to the higher aspect ratios when creating submicron features, which can result in fragile, error-prone fabrication. For example, a membrane with a thickness of 20 μm and pore diameters of 1 μm has an aspect ratio of 20.

As an example, the immune-isolation membrane 126 may be fabricated using a molding process with silicon microneedles (μ-needles). The μ-needle mold and the resulting pore structure in the membrane 126 includes a wide base and a narrow tip to support robust, repeatable molding and demolding cycles. Moreover, conical pores may increase diffusivity as compared to straight pores by up to about a factor of 20. The size of the base of the conical μ-needle and the widest part of the resulting pore in the membrane 126 is about 1 μm to about 20 μm. The size of the tip of the conical μ-needle and the narrowest part of the resulting pore in the membrane 126 is about 400 nm to about 5 μm, and preferably about 1 μm. The membrane 126 may be fabricated using the μ-needle mold using spin-casting and/or compression molding. As an example, liquid PDMS prepolymer may be spin cast or compression molded onto the μ-needle mold and then cured, resulting in a solid membrane with pore sizes determined by μ-needle tip sizes. The μ-needle mold may be fabricated using photolithographic mask techniques and/or isotropic and/or anisotropic etching. Etch rates and photolithographic mask designs can be altered to change the pore size, spacing and geometry in the membrane. The aspect ratios and geometries of the μ-needles can be varied to achieve desired levels of transport. For example, a steeper μ-needle uses alternating periods of isotropic and anisotropic etching, and closer needle spacing uses a tighter pattern on the photolithographic mask.

Example Method of Immune-Isolation Membrane Fabrication

Figure 2A:
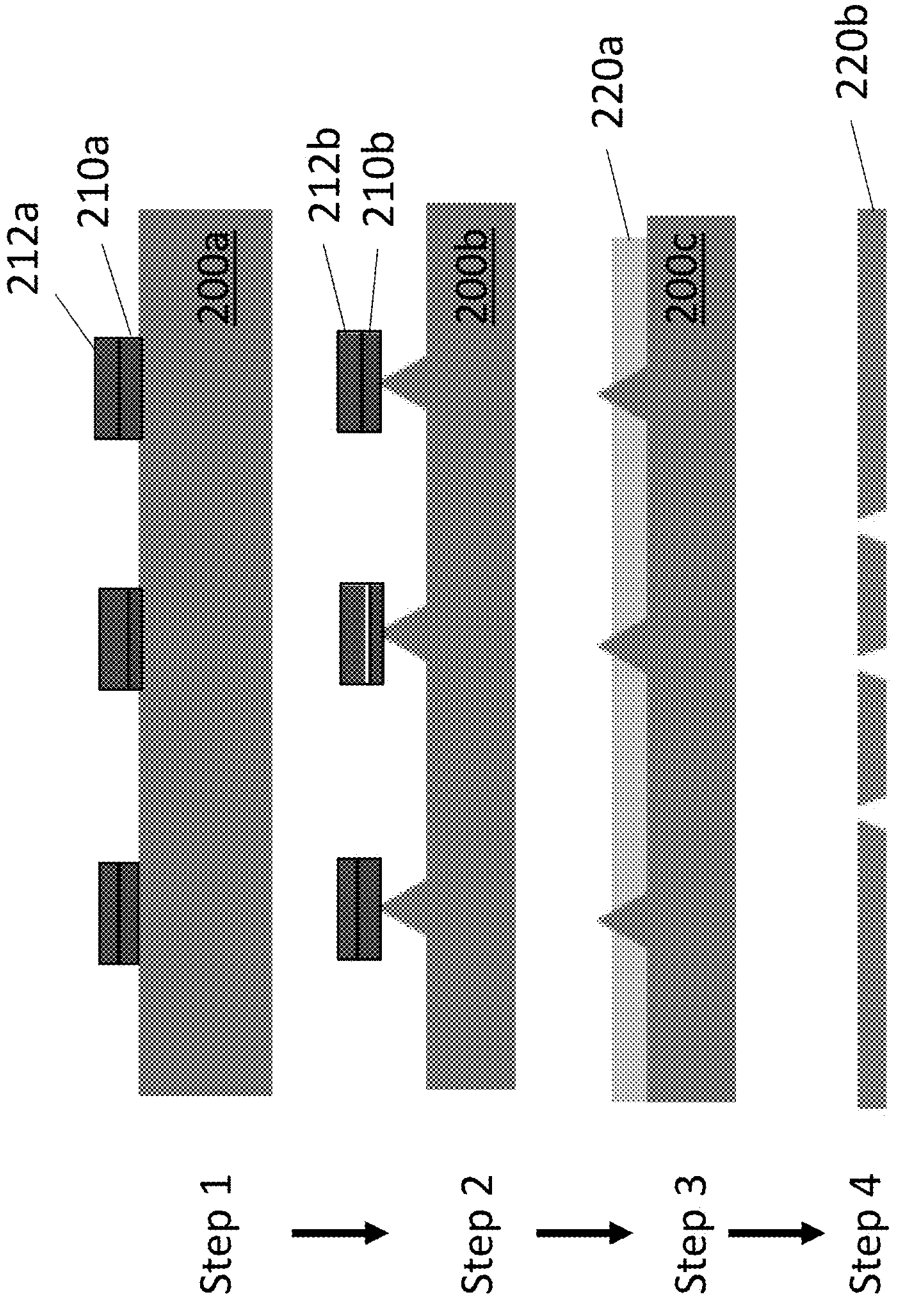
FIG. 2A illustrates a fabrication scheme to form a porous immune-isolation membrane.

FIG. 2A shows an example fabrication scheme to form a porous PDMS immune-isolation membrane. In step 1, the silicon wafer 200*a* having an SiO2 layer 210*a* with a thickness of about 200 nm deposited thereon is patterned with photoresist 212*a* and the SiO2 layer not protected by the photoresist 212*a* is etched. In step 2, the silicon wafer 200*b* is etched to create conical, cylindrical, or cuboid shaped microneedles formed in the silicon. Preferably, the pores have a conical shape because this shape offers several advantages, including a funneling effect to increase diffusion and ease of manufacturing. As an example of the manufacturing benefits afforded by conically shaped pores, a PDMS membrane may have a thickness of about 6 μm or greater and the pore size may be about 1 μm to exclude cells, and therefore an aspect ratio of at least about 6, which is too high for reliable PDMS membrane fabrication. Conical pores overcome this problem by providing a broad base and a narrow tip, decreasing the aspect ratio and affording higher reliability during PDMS membrane fabrication.

In step 3, the photoresist and SiO2 layers are removed, the wafer 200*c* is coated with a liquid PDMS prepolymer 220*a*, and then the prepolymer 220*a* is cured. The prepolymer 220*a* is a substance which represents an intermediate stage in polymerization and can be usefully manipulated before polymerization is completed. In step 4, the cured PDMS layer is removed from the silicon wafer 200*c* to result in the immune-isolation membrane 220*b*. In some embodiments, a thin film of polymethylmethacrylate (PMMA) may be spin-coated onto the silicon μ-needle mold and baked to create a hydrophobic surface suitable for PDMS molding prior to adding the PDMS prepolymer 220*a* in Step 3. Spin coating a PDMS layer onto the microneedle pattern in Step 3 at a carefully controlled speed (about 3000 rpm) can result in a reproducible film thickness matched to the height of the microneedles (about 20 μm). Applying gentle pressure with a hydrophobic sheet provides reproducible pore formation at the sharp needle tips. The resulting porous PDMS film can be reproducibly manufactured at pore sizes (about 600 nm to about 5 μm) and open areas appropriate for immunological protection and enhanced transport.

Figures 2B, 2C:
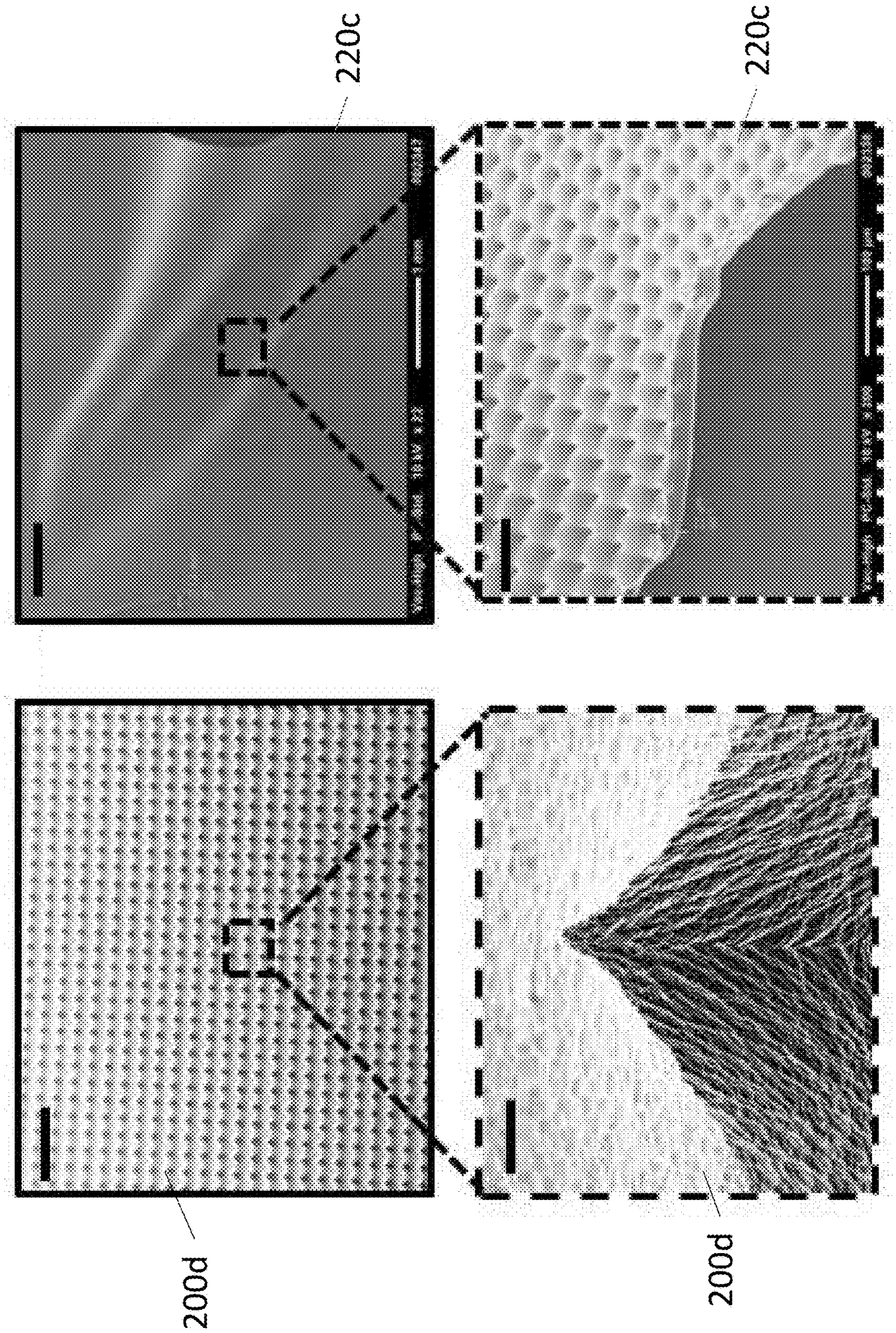
FIG. 2B is an electron microscope image showing a silicon microneedle template used to create a porous membrane using the scheme in FIG. 2A.
FIG. 2C is an electron microscope image showing a porous membrane made using the scheme in FIG. 2A.

FIG. 2B shows an example of the silicon μ-needle mold (also sometimes referred to as a template) used to create the porous immune-isolation membrane using the scheme in FIG. 2A. FIG. 2B shows an array of μ-needles (top) with a scale bar of 150 μm inset and a single μ-needle (bottom) in the array with a scale bar of 5 μm inset. FIG. 2C shows a porous membrane made using the scheme in FIG. 2A and the μ-needle mold shown in FIG. 2B. FIG. 2C shows the PDMS membrane (top) with a scale bar of 500 μm inset and a closer view of the PDMS membrane (bottom) showing the array of pores with a scale bar of 100 μm.

In another embodiment, the immune-isolation membrane includes another material instead of PDMS. For example, the membrane may be made of polyurethane and may be formed using a micromolding process similar to the one described above. As another example, the membrane may be track-etched polycarbonate (PCT) or polytetrafluoroethylene (PTFE) with pores having a size of about 200 nm to about 2000 nm (e.g., 800 nm).

Example Wireless Power Transfer

Figure 3A:
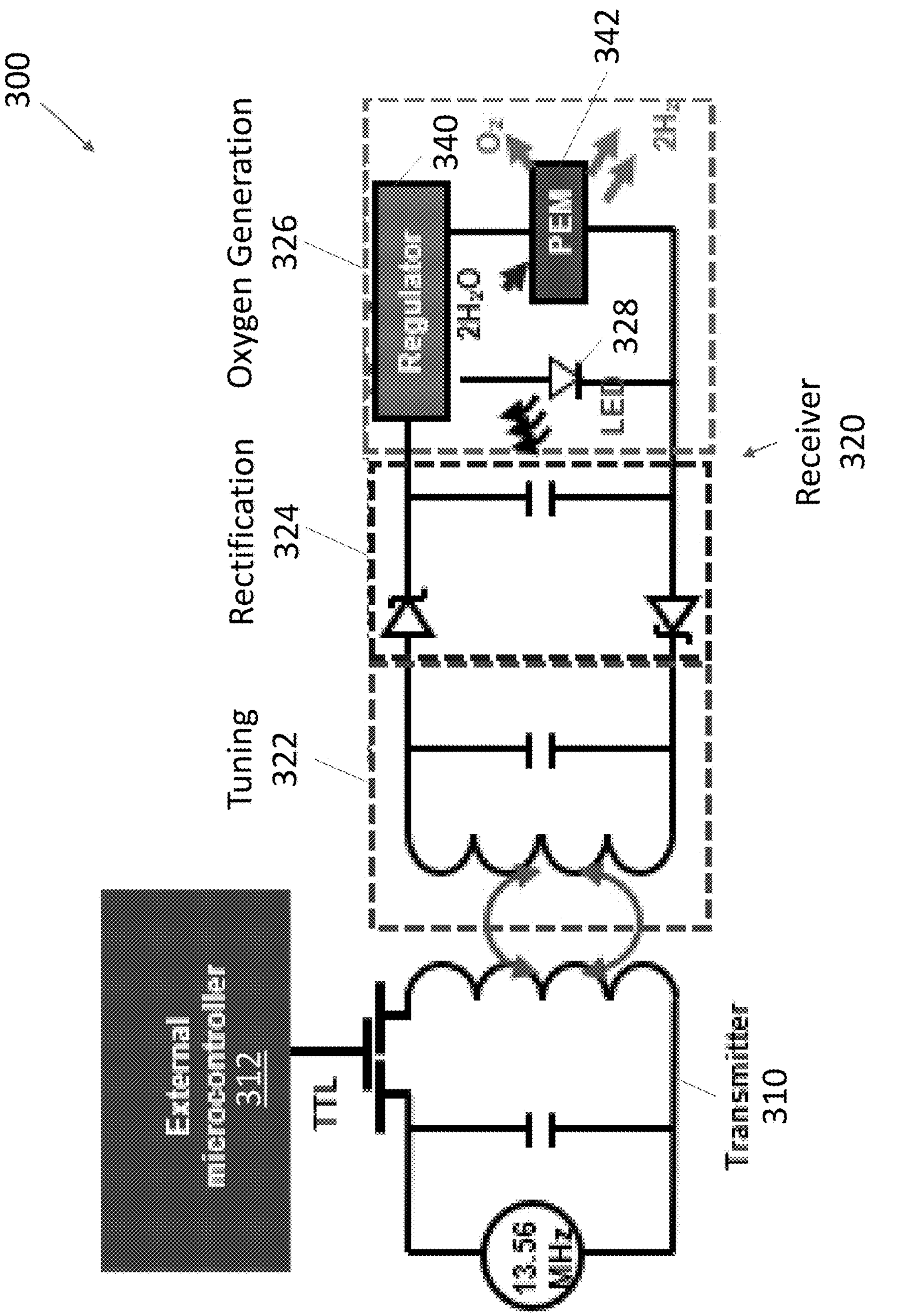
FIG. 3A illustrates an electrical schematic for a bioelectronic device for encapsulated cell therapies.

FIG. 3A shows a schematic of a wireless power transfer system that may be incorporated into the bioelectronic device to power the electrochemical cell. The board that supports the electrochemical cell also supports components supplying electrical power to the electrochemical cell. Components supplying electrical power may do so in a wired or wireless fashion, depending on the type of components used.

The power supply 300 shown in FIG. 3A harvests power wirelessly without a battery. The bioelectronic device is powered via resonant inductive coupling at a frequency of 13.56 MHz, a near-field communication frequency. Near-field communication possesses advantages in reliability, size, and simplicity. In one example, the entire receiver circuit 320 in the bioelectronic device weighs less than 1 gram. Additionally, 13.56 MHz has low specific absorption rates in biological tissue and can power implants up to a range of 4 mm away. The wireless power transfer approach involves two subassemblies: (1) an external transmitter circuit 310, and (2) an implantable receiver circuit 320. The external transmitter circuit 310 is part of a remote device and includes a waveform generator capable of producing an alternating current (AC) voltage at 13.56 MHz, connected to a power amplifier to achieve power levels of 10 W, and a transmitter coil. Capacitors and inductive antennae complete the LC circuit in the transmitter circuit 310 and allow for impedance matching to the receiver circuit 320. The external transmitter circuit 310 may include a signal generator capable of producing a sinusoidal AC waveform, a power amplifier, a power supply (e.g., a battery), and a transmitter antenna, all of which may be off-the-shelf components.

An external microcontroller 312 couples to the transmitter circuit 310 and provides pulsing power to the bioelectronic device based on transistor-transistor logic (TTL) at any desired frequency and duty cycle. A pulsed power mode can be used to fill the gas diffusion chamber in an energy efficient manner. The filling rate is controlled by the pulse frequency, pulse intensity, and duty cycle used to provide power to the electrochemical cell. The duty cycle can be varied between 0.01% and 50% (e.g., 0.01%, 0.05%, 0.1%, 0.5%, 1%, 5%, 10%, 20%, 30%, 40%, or 50%) and the frequency can be varied between 0.0002 Hz and 0.05 Hz (e.g., 0.0002 Hz, 0.0005 Hz, 0.0008 Hz, 0.001 Hz, 0.005 Hz, 0.01 Hz, 0.05 Hz, 0.1 Hz, or 0.5 Hz). As an example, the bioelectronic device used a duty cycle of 50% and a frequency of 0.00083 Hz (10 minutes on, 10 minutes off). As another example, the bioelectronic device may operate for a total of 1 hour per 24-hour cycle using any of the duty cycles and frequencies described above to fill the gas diffusion chamber.

The receiver circuit 320 in the implantable bioelectronic device includes a tuning circuit 322, a rectification circuit 324, and an oxygen generation circuit 326. The tuning circuit 322 includes an L-C oscillator with the inductance (L) and capacitance © tuned to be impedance-matched to the transmitter circuit 310. The tuning circuit 322 includes a tuning capacitor with a capacitance of about 1 picoFarad (pF) to about 200 pF. The rectification circuit 324 includes a buffering capacity with a capacitance of about 1 micro-Farad (μF) to about 10 μF. The inductor may have an inductance of about 500 nanHenries (nH) to about 15 microHenries (μH). The inductor may be custom-designed and constructed from a thin, dense, rolled copper laminate on a polyimide film. The width and thickness of the traces of the inductor and the number of turns in the inductor coil define the impedance values. The width of the inductor traces may be about 60 μm to about 80 μm (e.g., 75 μm) and the thickness may be about 15 μm to about 25 μm (e.g., 18 μm). The number of turns in the inductor may be about 6 to about 50 (e.g., 6, 10, 12, 24, 30, 36, 40, or 50) and may be placed on one side of the board or both sides of the board. In an example, the inductor includes 12 coils with 6 on the top of the board and 6 on the bottom of the board. In this way, the inductor is etched directly into the circuit board, and, owing to the thin construction of the board (e.g., a total thickness of Cu and polyimide layers of about 110 μm) the entire assembly is mechanically flexible owing to its low flexural rigidity (e.g., about 5 to about 10 N-m). A tuning capacitor in parallel with the inductor completes the impedance matched LC-circuit in the receiver circuit 320. The rectification circuit 324 includes surface-mounted (SMD) diodes and capacitors to complete rectification, while an SMD low-dropout regulator (LDO) ensures steady voltage output (e.g., at 2V), sufficient to power the oxygen generation circuit 326. The choice of LDO can be tuned to achieve any voltage up to an output voltage of about 5 V. The oxygen generation circuit 326 includes the electrochemical cell 342, a regulator 340, and a light-emitting diode (LED) or organic light-emitting diode (OLED) 328. The LED 328 may be used as a light stimulus to modulate the therapeutic cells in the bioelectronic device. A microcontroller may be embedded on the printed circuit board in the bioelectronic device to control the LED 328 and the electrochemical cell 342.

Light delivery by the LED 328 directly to the therapeutic cells in the cell housing chamber may activate gene circuits for dosed drug delivery. This approach is useful when the therapeutic cells are engineered to be responsive to light. The LED 328 may be a single diode or an array of LEDs on the circuit board. The LED 328 can be pulse-width and duty-cycle modulated to control the functioning of the therapeutic cells. The LED 328 is powered and controlled by the power supply 300 and/or a microcontroller in the bioelectronic device. Light intensity may be varied from about 1 $mW/mm^2$ to about 10 $mW/mm^2$ (e.g., 1 $mW/mm^2$, 2 $mW/mm^2$, 4 $mW/mm^2$, 5 $mW/mm^2$, 8 $mW/mm^2$, or 10 $mW/mm^2$), including all values and sub-ranges in between, the frequency may be varied by about 0.0001 Hz to about 0.01 Hz (e.g., 0.0001 Hz, 0.0005 Hz, 0.001 Hz, 0.005 Hz, or 0.01 Hz), including all values and sub-ranges in between, and the duty cycle can be varied by about 5% to about 50% (e.g., 5%, 10%, 20%, 25%, 30%, or 50%), including all values and sub-ranges in between, to vary protein secretion kinetics by the therapeutic cells. LED intensity is varied by a current-limiting resistor in series with the LED. Intensity can be increased by lowering the value of the current limiting resistor in series with the LED. Frequency and duty cycle are programmed into an onboard or external microcontroller. If the LED 328 is an array of LEDs, the microcontroller can multiplex the array of LEDs to sequentially address individual light-emitting diodes in the array. The array can be sequentially pulsed rapidly to increase the circumferential illumination space. The array may be pulsed at a low duty cycle for thermal management to prevent overheating.

Figure 3B:
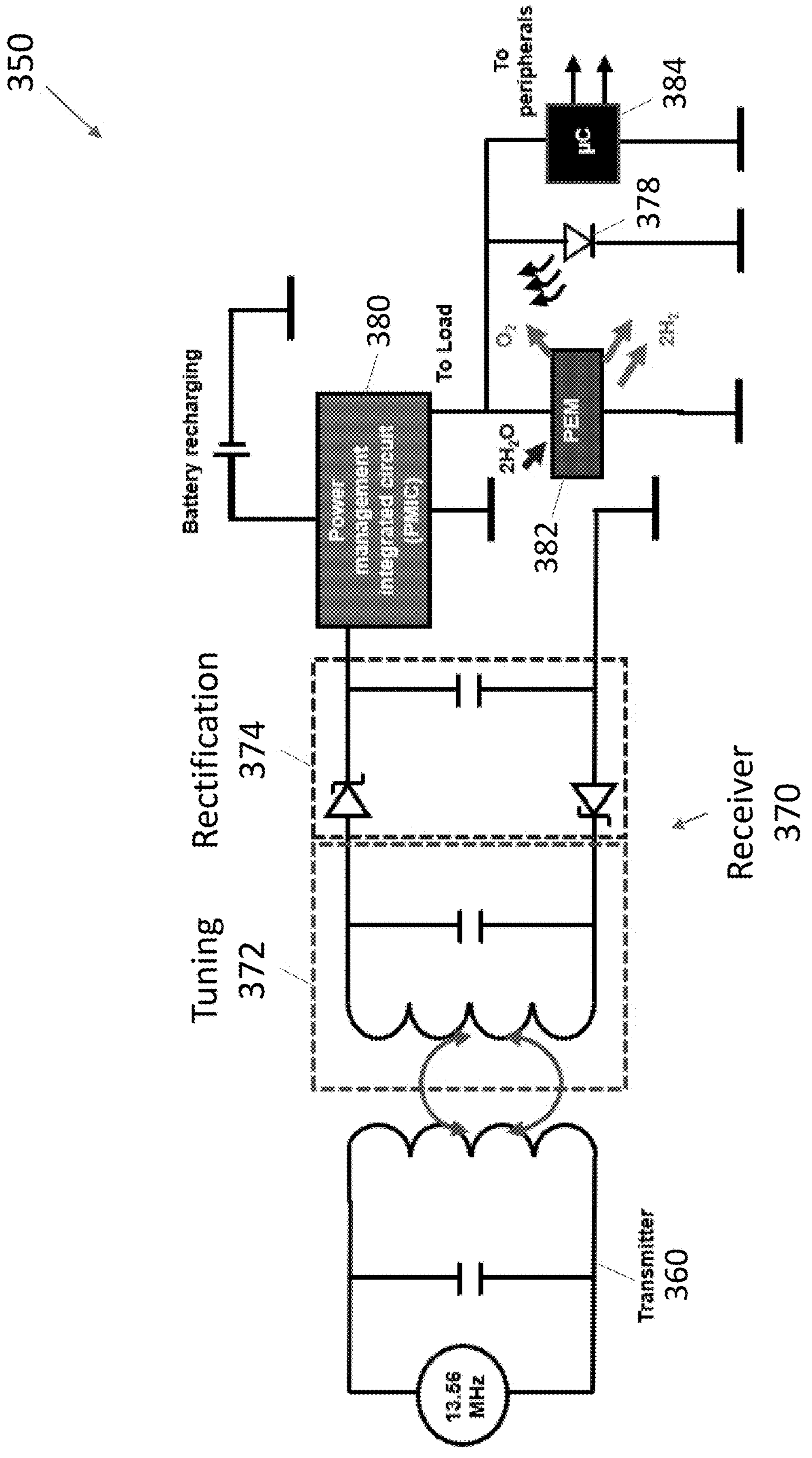
FIG. 3B illustrates another electrical schematic for a bioelectronic device for encapsulated cell therapies.

FIG. 3B shows another schematic of a wireless power system 350 that may be incorporated into the bioelectronic device to power the electrochemical cell. The wireless power system 350 shown in FIG. 3A has benefits in simplicity, size, and wight. The wireless power system 350 in FIG. 3B has benefits in its ability to support more complex electronic components that meet and increased power demand. The wireless power system 350 includes an external transmitter circuit 360 and an implantable receiver circuit 370. The external transmitter circuit 360 includes a waveform generator capable of producing an alternating current (AC) voltage at 13.56 MHz, connected to a power amplifier to achieve power levels of 10 W, and a transmitter coil. Capacitors and inductive antennae complete the LC circuit in the transmitter circuit 360 and allow for impedance matching to the receiver circuit 370. The receiver circuit 370 is in the bioelectronic device and includes a tuning circuit 372, a rectification circuit 374, a power management integrated circuit (PMIC) 380, a battery, and the electrochemical cell 382. The battery is a high-capacity, IEC60601 certified battery. The tuning circuit 372 includes an L-C oscillator with the inductance (L) and capacitance (C) tuned to be impedance-matched to the transmitter circuit 360. A tuning capacitor in parallel with the inductor completes the impedance matched LC-circuit in the receiver circuit 370. The rectification circuit 374 includes surface-mounted (SMD) diodes and capacitors to complete rectification, while an SMD low-dropout regulator (LDO) ensures steady voltage output (e.g., at 2V), sufficient to power electrochemical water electrolysis by the electrochemical cell 382. The choice of LDO can be tuned to achieve any voltage up to an output voltage of about 5 V. The receiver circuit 370 includes a PMIC 380 that manages battery charging, including overcharge protection and thermal management. The receiver circuit 370 also includes an LED 378 and a microcapacitor 384 to power peripheral electronic components (e.g., sensors).

The device may include sensors to provide insight into the functioning of the device. For example, one or more sensors may measure oxygen concentrations. The oxygen sensor(s) may be optical based on oxygen quenching or electrical (e.g., a Clark electrode). One or more sensors may also measure biomarkers to quantify device function. For example, the device may include a glucose sensor if it includes cells used to treat diabetes (e.g., islets or pancreatic beta cells). One or more sensors may also measure secreted proteins.

Figure 4A:
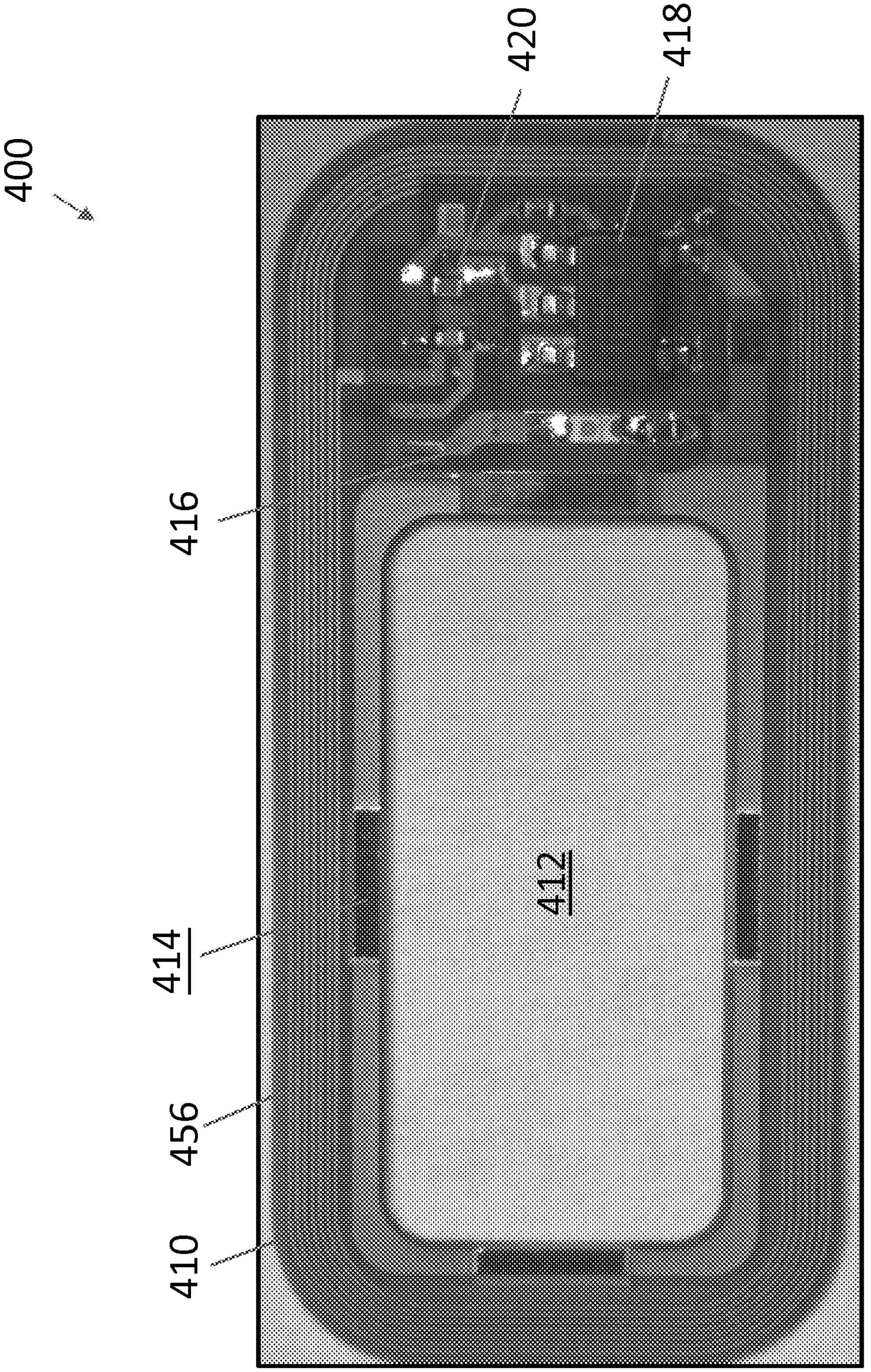
FIG. 4A is an image showing the electrical components in a bioelectronic device for encapsulated cell therapies.
Figure 4B:
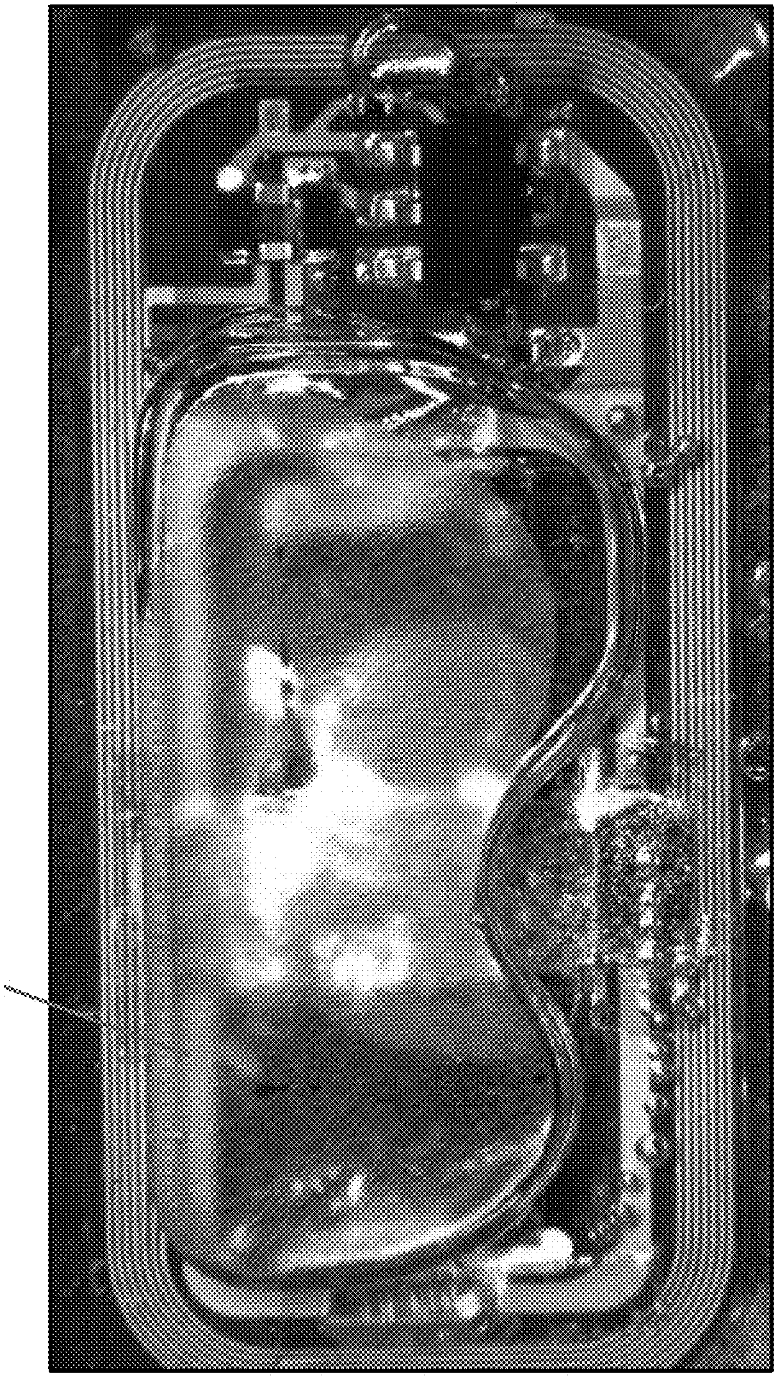
FIG. 4B is an image showing the device in FIG. 4A with a gas diffusion chamber on top of an electrode stack.

FIG. 4A shows an example of a flexible receiver circuit board 400. A cation-conducting membrane 412 for the electrochemical cell is mounted into the board 410. Four bond pads 414 act as electrical contact points for electrically coupling electrodes (not pictured) on either side of the membrane 412. The electrodes are adhered to the bond pads 414 via conductive adhesive bonding. The LDO 418 and the rectification and tuning circuitry 420 are disposed on the board 410 adjacent to the membrane 412. An LED 416 is also mounted to the board 410. Inductor 456 is an electrically conductive metal coil embedded in an insulating polymer. The inductor 456 is embedded in the board 410. FIG. 4B shows a gas diffusion chamber 422 mounted on top of the electrochemical cell in the receiver circuit board 400 shown in FIG. 4A. The gas diffusion chamber 422 receives oxygen gas generated by the electrochemical cell and stores it.

Figure 4D:
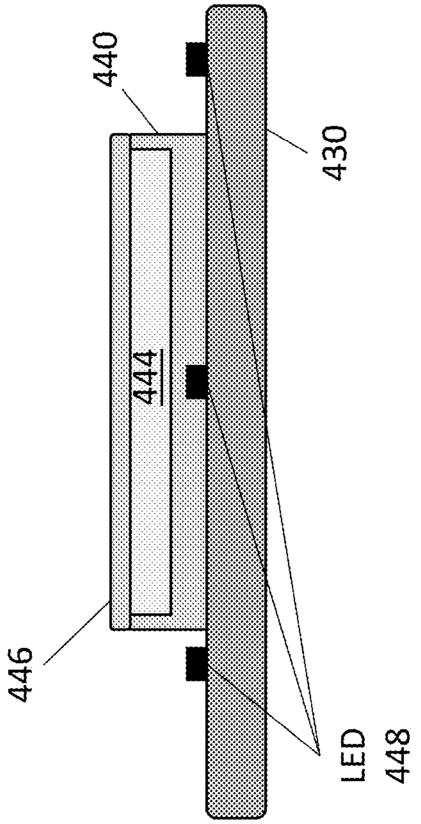
FIG. 4D illustrates a cross-sectional view of the bioelectronic device in FIG. 4C.
Figure 4C:
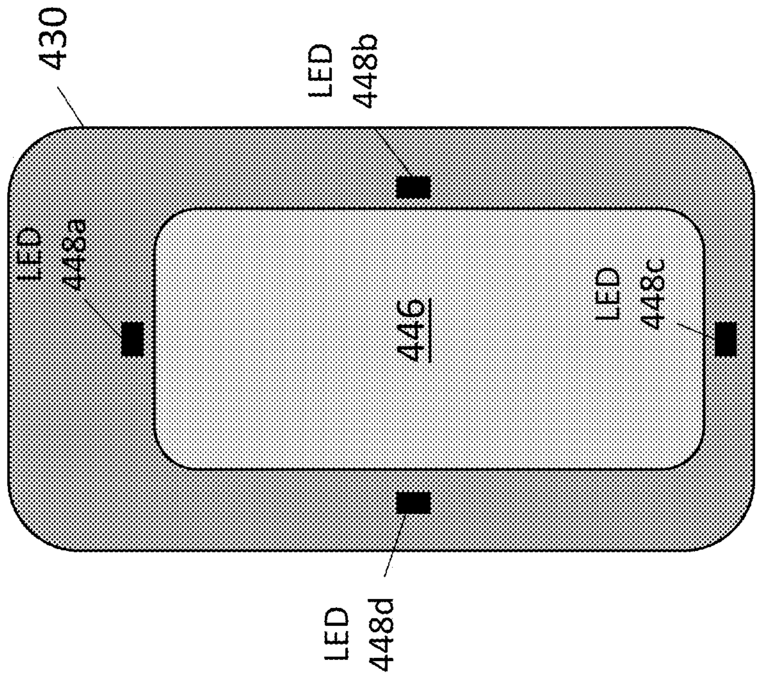
FIG. 4C illustrates a top view of a bioelectronic device having an array of LEDs.

FIGS. 4C and 4D illustrate a top view and a cross-sectional view, respectively, of a flexible PCB 430 having an array of LEDs 448*a*-448*d* (or OLEDs) disposed on the surface of the PCB 430 positioned around the cation-conducting membrane 446 to direct light into the cell housing chamber 444 to regulate secretion kinetics (e.g., activate or deactivate protein secretion from therapeutic cells). In this way, the LEDS 448a-448d regulate the delivery of therapeutic agents to the host through the cation-conducting membrane 446. LEDs 448a-448d may surround the cell housing chamber 444 circumferentially. The cell housing chamber's walls may be substantially transparent so that light from the LEDs 448a-448d may reach the cells. In another embodiment, miniaturized waveguides (e.g., made of silicon, PDMS, or glass) may be disposed on the PCB 430 to guide and direct light into the cell housing chamber 444. The microcontroller on the PCB 430 may be configured to multiplex the plurality of light-emitting diodes to sequentially address individual light-emitting diodes of the plurality of light-emitting diodes.

Example Method of Device Fabrication

FIG. 5A shows an example fabrication and assembly procedure for making the bioelectronic device. First, a flexible circuit board 510 is created or procured with an antenna embedded into it for wireless power harvesting. Then, electronic components (e.g., the power supply 518 and the LED 516) are added to the board 510 and electrically coupled together using reflow soldering. The electrochemical cell including the cation-conducting membrane 512 and electrodes 514a and 514b disposed on either side of the membrane 512 are attached to the board 510. After the electrochemical cell is added to the board 510, the board (including the electrochemical cell and other electronic components) is encapsulated in a silicone housing 520 via dip-coating. The silicone housing 520 has a thickness of about 0.5 mm to 1 mm. A gas diffusion chamber 522 made of silicone is attached to a side of the encapsulated board 510 near the electrochemical cell's anode at which oxygen is generated. The gas diffusion chamber 522 is attached to the housing 520 using silicone-silicone bonding or silicone adhesive. The cell housing chamber 524 having five sides is stacked on top of the gas diffusion chamber 522 on the side of the gas diffusion chamber 522 opposite the side adjacent to the board 510. An immune-isolation membrane 526 is attached to the top of the cell housing chamber 524 opposite the side of the cell housing chamber adjacent to the gas diffusion chamber 522 to enclose the cell housing chamber 524. The cell housing chamber 524 and immune-isolation membrane 526 are attached using silicone-silicone bonding or silicone adhesive.

Once the device is assembled, cells are loaded into the cell housing chamber 524. Cells may be loaded through loading ports located on the device using a syringe needle. The cells may be suspended in cell culture medium or an un-cross-linked hydrogel (including an extracellular matrix). The loading port may then be sealed using an adhesive glue that is fast-curing (e.g., fast-curing silicone glues) or UV-curable. If the cells are suspended in an un-crosslinked hydrogel, the hydrogel matrix may be crosslinked by immersing the device in a $Ca^{+}$ or $Ba^{+}$-rich bath to facilitate crosslinking and gelation. Cell loading may take place immediately prior to implantation.

FIG. 5B shows an example scheme to modify the surface of the bioelectronic device 500 with an anti-fibrotic coating. Conventionally, fibrosis induced by the foreign body response is a cause for encapsulated cell death in vivo. Previous trials using conventionally encapsulated used the administration of systemic immunosuppressants to patients to decrease risks associated with inflammation and fibrosis. In contrast, the bioelectronic device 500 can operate in the body without the use of immunosuppressants. An embodiment of the bioelectronic device 500 includes an anti-fibrotic coating that suppresses the formation of fibrotic tissue around the implanted device. The anti-fibrotic coating is a small molecule grafted onto one or more surfaces of the device that substantially reduces surface collagen deposition on the bioelectronic device. The coating may prevent or mitigate an accumulation of immune cells on the device, and/or the formation of scar tissue on the device. The anti-fibrotic coating can provide long-term biocompatibility in vivo. The anti-fibrotic coating may be disposed on all outer surfaces of the device, on some of the outer surfaces, or only on the immune isolating membrane.

The anti-fibrotic coating may include a zwitterionic polymer. The zwitterionic polymer may be a sulfobetaine polymer or a phosphocholine polymer. The zwitterionic polymer may be modified with a small molecule that helps prevent biofouling. The small molecule may be tetrahydropyran phenyl triazole (THPT), (4-(4-(((tetrahydro-2H-pyran-2-yl)oxy)methyl)-1H-1,2,3-triazol-1-yl)phenyl) phenyl triazole, or N-(4-((1,1-dioxidothiomorpholino)methyl)-1H-1,2,3-triazol-1-yl).

FIG. 5B shows a surface-initiated atom transfer radical polymerization (si-ATRP) scheme to graft polymer brushes modified with tetrahydropyran phenyl triazole (THPT), an anti-fibrotic molecule, onto one or more surfaces of the bioelectronic device 100, 130, and/or 150. In a version, every outer surface of the device is coated with THPT. The THPT coating thickness is about 10 nm to about 100 nm. In the first step 501, a surface of the bioelectronic device 500a (corresponding to device 100, 130, and/or 150 above) is reacted with a graft initiator 550 to create a bioelectronic device 500b coated with the graft initiator 550. In the second step 503, THPT (also called E9) molecules 552 are grafted onto the bioelectronic device 500c at the graft initiator sites to form the anti-fibrotic coating. This si-ATRP process is compatible with the components of the bioelectronic device. As an example, the bioelectronic device with THPTO grafted to the surface was completely free of fibrosis after 1 month of implantation. As an alternative to si-ATRP, THPT may be grafted onto the surface of the bioelectronic device using free radical polymerization of THPT-acrylate subjected to short plasma treatment or using polydopamine coating. Alternatively, GW2580 (CSF1 inhibitor) crystals may be loaded into the bioelectronic device along with the cells to prevent fibrosis. For example, 1 to 3 crystals may be loaded into a cell housing chamber in the device.

FIG. 5C shows the assembled bioelectronic device 500 (corresponding to device 100, 130, and/or 150 above) implanted into a host 590 in an example location in subcutaneous, intraperitoneal, or intramuscular tissue. The bioelectronic device 100, 130, and/or 150 can treat a broad range of diseases by replenishing defective of deficient proteins. For example, the device 100, 130, and/or 150 can be used to treat diabetes, anemia, autoimmune disorders, or blood clotting disorders. The device can also be used for cancer immunotherapy treatment using cells that secrete antibodies and/or cytokines. The device 100, 130, and/or 150 may also be used for the treatment of Parkinson's and Huntington's diseases. Therapeutic cells encapsulated in the bioelectronic device 100, 130, and/or 150 may be primary cells or cultured cells.

Therapeutic cells or other biological entities encapsulated in the bioelectronic device may be engineered to secrete precisely controlled doses of therapeutic agents on demand, allowing treatment of these complex diseases. The therapeutic cells may be primary human cells (e.g., hepatocytes, islets, mesenchymal stem cells, human dermal fibroblasts, neurons, or a combination thereof). The therapeutic cells may be cell lines (e.g., Human Embryonic Kidney (HEK) cells, ARPE cells, CHO-K1 cells, or a combination thereof). The therapeutic cells may be xenogeneic cells (e.g., pancreatic islets). The bioelectronic device may include a combination of different types of cells. For example, human embryonic kidney (HEK) cells engineered to secrete insulin can be encapsulated in the bioelectronic device to treat diabetes (Type 1 or Type 2) in a host. Retinal epithelial cells (e.g., ARPE-19) engineered to secrete Factor VIII may be encapsulated in the bioelectronic device for the treatment of hemophilia. Endothelial cells (e.g., HUVEC) engineered to secrete Factor IX may be encapsulated in the bioelectronic device also for the treatment of hemophilia. Human dermal fibroblasts may secrete neurotrophic factors for the treatment of neurological disorders including Alzheimer's, Huntington's, and Parkinson's diseases.

Primary cells may be sourced from human donor organs to provide functions of failing organs. For example, pancreatic islets (e.g., from a human or a pig) may be encapsulated in the bioelectronic device to provide functions of the pancreas (e.g., insulin production) for the treatment of diabetes. Other insulin-producing cell lines (e.g., insulinoma) may be used for the treatment of diabetes. Hepatocytes may be encapsulated to be used as liver organoids. Neurons may be encapsulated to provide functions of nervous tissue, including for the treatment of neurological disorders.

As an example, the bioelectronic device 100, 130, and/or 150 can house 20 million ARPE19 cells and keep them viable for 6 months in vivo. The 20 million cells can deliver up to 1 μg of protein per day to the host for the treatment of hemophilia A (HA). HA is a bleeding disorder affecting approximately 20,000 people in the US and 400,000 people worldwide. HA results from a mutation in factor VIII gene (FVIII) resulting in impaired clotting activity with patients having a high risk of life-threatening bleeding and serious complications, including joint and muscle diseases. No effective long-term treatment of HA exists because of the half-life of exogenous FVIII products is less than 24 hours. FVIII replacement through cell-based therapy is promising since relatively low amounts of circulating FVIII (<5% of physiological levels) can reduce the severity of the disease. The ARPE cell line is engineered to secrete FVIII and delivers FVIII over the long-term to the host using the bioelectronic device. The delivery of 1 μg of protein per day to the host from the bioelectronic device is 10-fold higher than the dosage of FVIII used clinically.

In summary, the bioelectronic device provides a microenvironment in which the therapeutic cells can live for an extended period. As an example, the bioelectronic device 100, 130, and/or 150 can be implanted in the host's body and deliver, continuously or intermittently, therapeutic agents to the host from live therapeutic cells encapsulated in the bioelectronic device 100, 130, and/or 150 for about 1 month to about 10 years (e.g., 1 month, 2 months, 3 months, 4 months, 5 months, 6 months, 1 year, 2 years, 5 years, or 10 years), including all values and sub-ranges in between.

Several types of cells may be encapsulated in the bioelectronic device 100, 130, and/or 150. For example, therapeutic cells that secrete therapeutic agents may be encapsulated in the bioelectronic device 100, 130, and/or 150, where the therapeutic agents can include therapeutic proteins and other biological products (e.g., antibodies, cytokines, growth factors, enzymes, immunomodulators, or thrombolytics). The therapeutic agent is delivered to a host (also sometimes referred to as a patient herein, e.g., a human or another animal) to treat one or more diseases, as described in more detail below. By increasing viability of the therapeutic cells implanted in the host, the bioelectronic device provides long-term treatment by the delivery of therapeutic agents to the host. Non-therapeutic cells may also be encapsulated in the bioelectronic device. For example, cells that regulate sleep cycles may be encapsulated in the bioelectronic device.

Large numbers of cells sufficient to supply therapeutic levels (e.g., minimum effective dose (MED), the lowest dose or concentration that produces a biological response, to the maximum tolerated dose (MTD), highest possible but still tolerable dose level with respect to a pre-specified clinical limiting toxicity) of a therapeutic agent can be encapsulated in the bioelectronic device. For example, the number of cells encapsulated in the device 100, 130, and/or 150 may be up to about 1 billion cells. The number of cells in the device 100, 130, and/or 150 may be selected based on the amount of therapeutic agent that is desired to be delivered to the host. The number of cells in the device influences the amount of therapeutic agent delivered to the host. For example, for the treatment of diabetes, over 350,000 islets (each islet contains many cells) may be used to treat an adult human. The amount of space required to house this many islets is prohibitive unless the islets are packed very closely together (e.g., 5000 islets $cm^{-2}$ or greater). It is not possible to keep islets viable while this closely packed using conventional devices. The secretion of therapeutic agents and/or delivery of the therapeutic agents to the host can be regulated by the bioelectronic device using heat stimulation, electrical stimulation, and/or light activation, as described in more detail below. In this way, the bioelectronic device 100, 130, and/or 150 controls the dose of therapeutic agent delivered to the host. Encapsulated cells may be primary cells that do not divide or may be immortalized dividing cells. Encapsulated immortalized cells may divide within the device to increase the number of encapsulated cells over time.

The bioelectronic device 100, 130, and/or 150 increases the long-term viability of therapeutic cells implanted in a host by generating oxygen in-situ for the therapeutic cells. The bioelectronic device 100, 130, and/or 150 provides an adequate supply of oxygen to encapsulated cells to prevent hypoxia mediated cell death. The bioelectronic device 100, 130, and/or 150 includes one or more electrochemical cells 113 and/ 133 that generate oxygen using electrolysis of water. This generation can maintain an oxygen partial pressure ($pO_2$) value of about 10% to about 70% (e.g., 10%, 11%, 12%, 13%, 14%, 16%, 18%, 20%, 30%, 40%, 50%, 60%, or 70%), including all values and sub-ranges in between, in the cell housing chamber 124, 144, and/or 164 holding the therapeutic cells. For example, the bioelectronic device 100, 130, and/or 150 can generate oxygen so that the $pO_2$ in the cell housing chamber 124, 144, and/or 164 is about 10% to about 13%, corresponding to values of dissolved oxygen (DO) in arterial blood.

The bioelectronic device 100, 130, and/or 150 expands the range of tissue types in which the therapeutic cells can be implanted to tissues that are oxygen-poor. Hypoxia mediated cell death can result from implanting therapeutic cells in oxygen-poor tissue or from fibrotic tissue formation around the implanted cells. As an example, the bioelectronic device 100, 130, and/or 150 can be located in an oxygen-poor environment (e.g., oxygen-poor tissue including subcutaneous tissue, an intraperitoneal space, an intracranial space, an intraocular space, or an intramuscular space) and still maintain high cell viability as if the therapeutic cells were in a naturally oxygen-rich environment.

Hypoxia mediated cell death can also result from fibrotic tissue formation around the implanted cells. Even a small fibrotic capsule around the cells can result in a significant diffusion barrier for implanted cells, resulting in local hypoxia and cell death. The bioelectronic device can be configured to counteract some of the negative effects of fibrosis. Fibrosis, induced by the foreign body response, is a cause of therapeutic cell death in vivo. Fibrotic tissue can form around the therapeutic cells to reduce or substantially prevent diffusion of oxygen from the host to the cells. The bioelectronic device 100, 130, and/or 150 prevents or substantially reduces hypoxia mediated cell death in at least the following ways. First, the bioelectronic device 100, 130, and/or 150 encapsulates the therapeutic cells and isolates them from fibrotic tissue formation. Second, the bioelectronic device 100, 130, and/or 150 generates its own oxygen supply for the therapeutic cells so that even if fibrotic tissue forms around the device and prevents the diffusion of oxygen from the host to the therapeutic cells, the cells do not experience hypoxia because the generated oxygen creates an oxygen-rich microenvironment in the chamber encapsulating the cells.

In addition to generating its own oxygen, in some embodiments the bioelectronic device 100, 130, and/or 150 also counteracts the negative effects of fibrosis using an anti-fibrotic coating on the outer surface of the device and/or on the device's semi-permeable immune-isolation membrane 126, 146, and/or 166. For example, the anti-fibrotic coating may include a small molecule tetrahydropyran phenyl triazole (THPT) which substantially reduces surface collagen deposition on the bioelectronic device once implanted. Zwitterionic polymers and/or drug eluting crystals may be used to prevent or substantially reduce fibrosis around the device.

Example Characterization of a Bioelectronic Device

FIG. 6A shows current measured during a voltage sweep of the electrochemical cell in an example bioelectronic device with calculated $O_2$ generation rates varying with voltage from 1.2 V to 2.0 V. The electrochemical cell used a PEM cation-conducting membrane and graphite electrodes. The dashed line represents the $O_2$ consumption rate (OCR) estimated for a therapeutic dose of islets encapsulated in the bioelectronic device and implanted in an adult human. The results show increasing applied voltage between 1.23 V and 2 V results in increasing current and $O_2$ generation rates.

FIG. 6B shows $O_2$ concentrations measured by an optical sensor above the electrochemical cell after being placed in a specialized hypoxic cell incubation chamber having an oxygen partial pressure of about 5% $O_2$ (a hypoxic condition) and subsequent operation of the electrochemical cell at 2 V. While operating, the electrochemical cell can rapidly (e.g., in less than 20 minutes) increase $O_2$ levels from less than about 2% to more than 45% in the chamber while maintaining low current (e.g., less than 4 mA) operation.

FIGS. 7A and 7B shows measurements of current received by the bioelectronic device across a standard mouse enclosure (10 cm×22 cm) at a height of 3.7 cm and 4.8 cm, respectively, corresponding to animal height at a load of 1000 ohm. The bioelectronic device used the electrical system shown in FIG. 3A to harvest power wirelessly. The system exhibited stable output current at 1000 ohms across the entire enclosure at both heights, allowing for robust operation in awake, freely moving hosts.

FIG. 7C shows measurements of received voltage and power using the inductor in the bioelectronic device as a function of load. The bioelectronic device used the electrical system shown in FIG. 3A to harvest power wirelessly with an inductor made of rolled copper laminate on a polyimide film. The inductor traces had a width of 75 μm, a thickness of 18 μm and there were 12 turns (6 each on the top and bottom sides of the board) in the inductor's coil. The results in FIG. 7C show that an example embodiment of the wireless electrical system higher power transfer efficiency at loads corresponding to a hydrated PEM having a surface area of about 1 $cm^2$ area, which has a resistive load between 600Ω and 1000Ω.

FIG. 7D shows measured current and computed oxygen production by the example bioelectronic device at different current values as a function of load. The measured currents at a range of load resistances corresponded to a peak measured current at the same load range as a PEM having a surface area of about 1 $cm^2$ (between 600Ω and 1000Ω), with a computed oxygen generation rate of up to 30 nmol/s. As an example, this oxygen generation rate is sufficient to maintain a clinically relevant islet population (~350,000 islet equivalent, IEQ) for human transplantation.

FIG. 7E compares $O_2$ production rates of wired and wireless bioelectronic devices as measured with a commercially available $O_2$ sensor in gas diffusion chamber. The wireless bioelectronic device using the electrical system shown in FIG. 3A exhibits equivalent performance in $O_2$ generation rates as compared to the wired system.

FIG. 7F shows pulsed mode operation of the bioelectronic device following an initial filling period, maintaining $O_2$ levels at about 45% at 50% duty cycle operation. The electrical system in FIG. 3A includes TTL, which provides pulsed-mode operation. Pulsed mode operation can be used to maintain $O_2$ levels at desired concentrations in the cell housing chamber and in the gas diffusion chamber in an energy efficient manner. Pulsed mode operation may be controlled using oxygen sensor input measuring the oxygen partial pressure in the cell housing chamber.

FIG. 8A shows results of an in vitro study comparing HEK-293 cells with a hypoxic fluorescent marker encapsulated in an example bioelectronic device as compared to the same type of cells not encapsulated. FIG. 8A shows mean fluorescence intensity (MFI) for naked (not encapsulated) cells (NC) and cells encapsulated in a bioelectronic device (EC) after 12 hours in a chamber having an oxygen partial pressure of 1% $pO_2$, a hypoxic condition, with and without the bioelectronic device electrochemically generating $O_2$. The results are compared to cells held in a control condition for 24 hours, specifically a chamber having an oxygen partial pressure of 21% $pO_2$, a normoxic condition. n=3 devices for all groups with error bars representing standard deviations. These results suggest the feasibility of the bioelectronic device to generate local $O_2$ to keep HEK-293 cells alive and non-hypoxic even in extremely hypoxic conditions.

FIG. 8B shows flow-assisted cell sorting (FACS) measurements comparing islet cells encapsulated in an example bioelectronic device as compared to the same type of cells not encapsulated. Cells encapsulated in the bioelectronic device (EC) were compared to cells not encapsulated (NC). Encapsulated cells were compared in two groups—one where the bioelectronic device generated oxygen and one where the bioelectronic device did not. The cells were incubated for 72 hours in a chamber having an oxygen partial pressure of 1% $pO_2$, a hypoxic condition, or in a chamber having an oxygen partial pressure of 21%, a normoxic condition. Cells in both the encapsulated and non-encapsulated conditions were much less viable after incubation in hypoxic conditions as compared to those incubated under normoxic conditions or under hypoxic conditions with oxygen generation by the bioelectronic device. These results suggest the feasibility of the bioelectronic device to generate local $O_2$ to keep islet cells alive and non-hypoxic even in extremely hypoxic conditions.

FIG. 8C shows glucose responsive insulin secretion (GSIS) at 2 glucose concentrations (2 mM, 20 mM) for encapsulated (EC) and naked (NC) pancreatic rat islets after incubation in 1% $O_2$ for 72 hours with supplemental $O_2$ generation in one hypoxic group. n=3 and error bars represent standard deviations. When exposed to a glucose concentration of 20 mM, the rat islets generated insulin. The amount of insulin generated by islets encapsulated in the bioelectronic device under hypoxic conditions but with the bioelectronic device generating oxygen for the islets was similar to the islets in the normoxic condition. As a comparison, the islets, both encapsulated and not, in the hypoxic conditions without any supplemental oxygen generation had markedly lower insulin secretion levels. These in vitro results indicate that encapsulated cells with the bioelectronic device generating oxygen maintain not only their viability but also their functionality as if in a normoxic condition.

FIG. 9 shows in vivo validation of an example bioelectronic device. FIG. 9 shows serum erythropoietin (EPO) levels measured before and 2 weeks after transplantation of the bioelectronic device holding human embryonic kidney (HEK-293) cells modified to secrete EPO. This in vivo validation involved the implantation of wireless, battery-free bioelectronic devices into the subcutaneous region of healthy, immunocompetent mice. No immune-suppressing medication was administered to the mice during the experiment. The bioelectronic devices had power harvesting electronics and external transmitter coils as described in FIG. 3A. Cell housing chambers in these devices were loaded with $5\times10^6$ human embryonic kidney (HEK-293) cells modified to secrete erythropoietin (EPO), a blood-borne protein that can be detected via plate-based assay techniques (e.g., ELISA). Control devices containing an identical number of cells were implanted into the subcutaneous space of immunocompetent mice, but without any oxygen generating electronics. Following transplantation, oxygen generation by the bioelectronic devices resulted in significantly increased protein production for two weeks, suggested its importance in maintaining cell viability, with protein production levels at 7× and 2.5× those of the controls at weeks 1 and 2 after implementation, respectively (n=4 for $O_2$ group, n=5 for control group). Regular bleeds on a single animal without any device implant showed no effect of bleeding on raising EPO levels. All animals were healthy, alert, and reactive for the duration of the experiment, displaying no adverse reactions and maintaining healthy, stable weights.

FIG. 10A shows serum EPO levels measured after implantation of a bioelectronic device holding human embryonic kidney (HEK-293) cells modified to secrete EPO and coated with an anti-fibrotic coating. The bioelectronic device in this example did not include any of the electronic or electrochemical components and did not generate its own oxygen supply. The presence of the anti-fibrotic coating, even without oxygen generation, substantially increased cell survival over the 4-week period of implantation in subcutaneous tissue. FIG. 10B shows the results in FIG. 10A compared to the results in FIG. 9 and indicate that a bioelectronic device that generates its own oxygen supply and has an anti-fibrotic coating on its surface can substantially improve encapsulated cell viability and function over a 4-week period of implantation in a host.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain, using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of" "only one of" or "exactly one of." "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A device for implantation in a subject, the device comprising:

an electrochemical cell, configured to produce oxygen gas from water when a voltage is applied across the electrochemical cell, the electrochemical cell comprising:
- a cathode;
- an anode; and
- a first membrane disposed between the cathode and the anode, wherein the first membrane is configured to permit passage of cations therebetween;

a circuit electrically coupled to the electrochemical cell and configured to provide power to the electrochemical cell, wherein the circuit is configured to receive power wirelessly from a remote device;

a chamber coupled to the electrochemical cell to receive at least a portion of the oxygen gas produced by the electrochemical cell; and a reservoir configured to hold a set of biological entities, wherein the reservoir is configured to receive the oxygen gas from the chamber for consumption by the set of biological entities, wherein a second membrane forms a portion of the reservoir, and the second membrane is permeable to one or more substances generated by the set of biological entities for delivery of the one or more substances to the subject via the second membrane, wherein the electrochemical cell, the chamber, and the reservoir are disposed together within a housing, and wherein the reservoir is stacked directly on top of the chamber on a side of the chamber opposite from the anode.

2. The device of claim 1, wherein the circuit comprises a circuit board, which comprises at least two bond pads disposed thereon, and wherein the circuit is electrically coupled to the electrochemical cell via conductive adhesive bonding between at least part of a surface of the cathode and a first bond pad of the at least two bond pads, and at least part of a surface of the anode and a second bond pad of the at least two bond pads.

3. The device of claim 2, wherein the circuit further comprises:

at least one light-emitting diode disposed on the circuit board and optically coupled to the reservoir, wherein the at least one light-emitting diode is configured to generate a light beam to enhance or modulate a function of the set of biological entities; and a microcontroller disposed on the circuit board and configured to modulate a pulse intensity, a pulse frequency, a duty cycle, or a combination thereof, of the at least one light-emitting diode.

4. The device of claim 3, wherein the at least one light-emitting diode comprises a plurality of light-emitting diodes optically coupled to the reservoir, and wherein the microcontroller is configured to multiplex the plurality of light-emitting diodes to sequentially address individual light-emitting diodes of the plurality of light-emitting diodes.

5. The device of claim 3, wherein the circuit further comprises a rechargeable battery, wherein the microcontroller and the rechargeable battery are collectively configured to store the received power to the rechargeable battery and to provide the power stored in the rechargeable battery to the electrochemical cell.

6. The device of claim 3, further comprising an oxygen sensor disposed in the reservoir or the chamber and communicably coupled to the microcontroller, wherein the microcontroller is further configured to modulate operation of the at least one light-emitting diode to maintain, based on an oxygen level detected by the oxygen sensor, the oxygen level in the reservoir or the chamber within a predetermined range.

7. The device of claim 1, further comprising a coating disposed on at least the second membrane, the coating including an anti-fibrotic substance.

8. The device of claim 1, wherein the second membrane is further permeable to oxygen and nutrients.

9. The device of claim 1, wherein the second membrane comprises at least one of polydimethylsiloxane or polycarbonate.

10. The device of claim 1, wherein the second membrane comprises a plurality of pores having a surface coverage of at least 5% of a total surface area of the second membrane, each pore of the plurality of pores independently having a pore diameter of from about 20 nm to about 5 μm.

11. The device of claim 1, wherein the chamber comprises at least one port to provide fluid communication between a fluid within the chamber and a biological fluid of the subject.

12. The device of claim 1, wherein the chamber comprises liquid water disposed therein and the chamber is sealed to prevent fluid communication with fluids outside the chamber.

13. The device of claim 1, wherein the device does not comprise a battery or an external oxygen supply.

14. The device of claim 1, wherein the chamber is configured to maintain an oxygen partial pressure of about 30 kilopascals to about 50 kilopascals during operation.

15. The device of claim 1, wherein the set of biological entities comprises at least one of primary human cells, stem cell derived cells, cell lines, or xenogeneic cells.

16. The device of claim 15, wherein:

the primary human cells include at least one of hepatocytes, islets, mesenchymal stem cells, human dermal fibroblasts, or neurons;

the cell lines include at least one of Human Embryonic Kidney (HEK) cells, ARPE cells, or CHO-K1 cells; and the xenogeneic cells comprise pancreatic islets.

17. The device of claim 1, wherein the anode and the cathode each comprise at least one of platinum, gold, carbon, iridium, or an oxygen-containing compound.

18. A device for implantation in a subject, the device comprising:

an electrochemical cell, configured to produce oxygen gas from water when a voltage is applied across the electrochemical cell, the electrochemical cell comprising:

a cathode;

an anode; and a first membrane disposed between the cathode and the anode, wherein the first membrane is configured to permit passage of cations therebetween;

a circuit electrically coupled to the electrochemical cell and configured to provide power to the electrochemical cell, wherein the circuit is configured to receive power wirelessly from a remote device;

a chamber coupled to the electrochemical cell to receive at least a portion of the oxygen gas produced by the electrochemical cell; and a reservoir configured to hold a set of biological entities, wherein the reservoir is configured to receive the oxygen gas from the chamber for consumption by the set of biological entities, wherein a second membrane forms a portion of the reservoir, and the second membrane is permeable to one or more substances generated by the set of biological entities for delivery of the one or more substances to the subject via the second membrane, and a coating disposed on at least the second membrane, wherein the coating includes an anti-fibrotic substance, wherein the coating comprises a zwitterionic compound which comprises at least one of sulfobetaine or phosphocholine polymer modified with at least one of tetrahydropyran phenyl triazole (THPT), (4-(4-(((tetrahydro-2H-pyran-2-yl)oxy)methyl)-1H-1,2,3-triazol-1-yl)phenyl)phenyl triazole, or N-(4-((1,1-dioxidothiomorpholino)methyl)-1H-1,2,3-triazol-1-yl).

19. A device for implantation in a subject, the device comprising:

an electrochemical cell, configured to produce oxygen gas from water when a voltage is applied across the electrochemical cell, the electrochemical cell comprising:

a cathode;

an anode; and a first membrane disposed between the cathode and the anode, wherein the first membrane is configured to permit passage of cations therebetween;

a circuit electrically coupled to the electrochemical cell and configured to provide power to the electrochemical cell, wherein the circuit is configured to receive power wirelessly from a remote device;

a chamber coupled to the electrochemical cell to receive at least a portion of the oxygen gas produced by the electrochemical cell; and a reservoir configured to hold a set of biological entities, wherein the reservoir is configured to receive the oxygen gas from the chamber for consumption by the set of biological entities, wherein a second membrane forms a portion of the reservoir, and the second membrane is permeable to one or more substances generated by the set of biological entities for delivery of the one or more substances to the subject via the second membrane, wherein the electrochemical cell, the chamber, and the reservoir are disposed together within a housing, and where the reservoir and the chamber share a wall bounding each of the reservoir and the chamber.

* * * * *